United States Patent
Moumene et al.

(10) Patent No.: US 9,232,968 B2
(45) Date of Patent: Jan. 12, 2016

(54) POLYMERIC PEDICLE RODS AND METHODS OF MANUFACTURING

(75) Inventors: Missoum Moumene, Newton, MA (US); Jonathan Fanger, Raynham, MA (US); Charles M Bartish, Jr., Providence, RI (US); Michael J. O'Neil, West Barnstable, MA (US); Anwar Upal, Fall River, MA (US); Stephen Connolly, Sharon, MA (US); John Riley Hawkins, Cumberland, MA (US); Michael A. Slivka, Taunton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 794 days.

(21) Appl. No.: 12/234,091

(22) Filed: Sep. 19, 2008

(65) Prior Publication Data

US 2009/0163955 A1 Jun. 25, 2009

Related U.S. Application Data

(60) Provisional application No. 61/014,851, filed on Dec. 19, 2007.

(51) Int. Cl.
*A61B 17/70* (2006.01)
*A61B 17/00* (2006.01)

(52) U.S. Cl.
CPC .......... *A61B 17/7031* (2013.01); *A61B 17/701* (2013.01); *A61B 17/7037* (2013.01); *A61B 17/7011* (2013.01); *A61B 2017/00526* (2013.01)

(58) Field of Classification Search
CPC ............. A61B 17/701; A61B 17/7011; A61B 17/7019; A61B 17/7029; A61B 17/7031
USPC ................. 606/246, 254, 255, 257, 259, 262
See application file for complete search history.

(56) References Cited

U.S. PATENT DOCUMENTS

| | | | |
|---|---|---|---|
| 3,992,725 | A | 11/1976 | Homsy |
| 4,512,038 | A | 4/1985 | Alexander |
| 4,648,388 | A | 3/1987 | Steffee |
| 4,743,260 | A | 5/1988 | Burton |
| 4,854,304 | A | 8/1989 | Zielke |
| 5,002,542 | A | 3/1991 | Frigg |
| 5,034,011 | A | 7/1991 | Howland |
| 5,092,866 | A | 3/1992 | Breard |
| 5,180,393 | A | 1/1993 | Commarmond |

(Continued)

FOREIGN PATENT DOCUMENTS

| | | |
|---|---|---|
| EP | 46518 | 7/1983 |
| EP | 470660 | 7/1995 |

(Continued)

OTHER PUBLICATIONS

Search Report dated Sep. 11, 2012 from EP08868340.

(Continued)

*Primary Examiner* — Jerry Cumberledge

(57) ABSTRACT

A spinal pedicle rod comprising an internally reinforced polymeric core that is at least partially encased within at least one polymeric coating. A dynamic stabilization device for bones in which flexible rods are combined with a pair of dynamic anchoring devices comprising i) a shank for anchoring into a bone or a vertebra, ii) a head connected to the shank, iii) a receiving part for the head and iv) a mobile element acting on the head.

8 Claims, 16 Drawing Sheets

(56) References Cited

U.S. PATENT DOCUMENTS

| | | |
|---|---|---|
| 5,181,930 A | 1/1993 | Dumbleton |
| 5,207,678 A | 5/1993 | Harms |
| 5,217,461 A | 6/1993 | Asher |
| 5,217,497 A | 6/1993 | Mehdian |
| 5,282,863 A * | 2/1994 | Burton .......................... 606/254 |
| 5,344,422 A | 9/1994 | Frigg |
| 5,360,431 A | 11/1994 | Puno |
| 5,375,823 A | 12/1994 | Navas |
| 5,387,213 A | 2/1995 | Breard |
| 5,403,314 A | 4/1995 | Currier |
| 5,415,661 A | 5/1995 | Holmes |
| 5,423,816 A | 6/1995 | Lin |
| 5,429,639 A | 7/1995 | Judet |
| 5,474,555 A | 12/1995 | Puno |
| 5,486,174 A | 1/1996 | Fournet-Fayard |
| 5,496,321 A | 3/1996 | Puno |
| 5,520,689 A | 5/1996 | Schlapfer |
| 5,540,688 A | 7/1996 | Navas |
| 5,540,689 A | 7/1996 | Sanders |
| 5,562,660 A | 10/1996 | Grob |
| 5,562,663 A | 10/1996 | Wisnewski |
| 5,562,737 A | 10/1996 | Graf |
| 5,630,817 A | 5/1997 | Rokegem |
| 5,643,260 A | 7/1997 | Doherty |
| 5,658,286 A | 8/1997 | Sava |
| 5,672,175 A | 9/1997 | Martin |
| 5,672,176 A | 9/1997 | Biedermann |
| 5,683,390 A | 11/1997 | Metz-Stavenhagen |
| 5,702,395 A | 12/1997 | Hopf |
| 5,704,936 A | 1/1998 | Mazel |
| 5,704,937 A | 1/1998 | Martin |
| 5,728,098 A | 3/1998 | Sherman |
| 5,733,284 A | 3/1998 | Martin |
| 5,738,685 A | 4/1998 | Halm |
| 5,782,833 A | 7/1998 | Haider |
| 5,797,910 A | 8/1998 | Martin |
| 5,851,006 A | 12/1998 | Spillner |
| 5,879,350 A | 3/1999 | Sherman |
| RE36,221 E | 6/1999 | Breard |
| 5,954,725 A | 9/1999 | Sherman |
| 5,961,516 A | 10/1999 | Graf |
| 6,004,349 A | 12/1999 | Jackson |
| 6,022,350 A | 2/2000 | Ganem |
| 6,053,917 A | 4/2000 | Sherman |
| 6,063,090 A | 5/2000 | Schlapfer |
| 6,077,262 A | 6/2000 | Schlapfer |
| 6,083,226 A | 7/2000 | Fiz |
| 6,099,528 A * | 8/2000 | Saurat .......................... 606/254 |
| 6,102,912 A | 8/2000 | Cazin |
| 6,139,549 A | 10/2000 | Keller |
| 6,224,598 B1 | 5/2001 | Jackson |
| 6,241,730 B1 | 6/2001 | Alby |
| 6,248,105 B1 | 6/2001 | Schläpfer |
| 6,251,112 B1 | 6/2001 | Jackson |
| 6,267,764 B1 | 7/2001 | Elberg |
| 6,273,888 B1 | 8/2001 | Justis |
| 6,293,949 B1 | 9/2001 | Justis |
| 6,302,888 B1 | 10/2001 | Mellinger |
| 6,361,535 B2 | 3/2002 | Jackson |
| 6,371,957 B1 | 4/2002 | Amrein |
| 6,379,356 B1 | 4/2002 | Jackson |
| 6,402,750 B1 | 6/2002 | Atkinson |
| 6,402,752 B2 | 6/2002 | Schaffler-Wachter |
| 6,440,132 B1 | 8/2002 | Jackson |
| 6,471,705 B1 | 10/2002 | Biedermann |
| 6,485,491 B1 | 11/2002 | Farris et al. |
| 6,520,963 B1 | 2/2003 | McKinley |
| 6,540,749 B2 | 4/2003 | Schäfer |
| 6,554,831 B1 | 4/2003 | Rivard |
| 6,595,993 B2 | 7/2003 | Donno |
| 6,626,908 B2 | 9/2003 | Cooper |
| 6,641,586 B2 | 11/2003 | Varieur |
| 6,645,207 B2 | 11/2003 | Dixon |
| 6,652,526 B1 | 11/2003 | Arafiles |
| 6,695,843 B2 | 2/2004 | Biedermann |
| 6,723,100 B2 | 4/2004 | Biedermann |
| 6,726,687 B2 | 4/2004 | Jackson |
| 6,730,089 B2 | 5/2004 | Jackson |
| 6,755,829 B1 | 6/2004 | Bono |
| 6,761,719 B2 | 7/2004 | Justis |
| 6,783,527 B2 | 8/2004 | Drewry |
| 6,786,903 B2 | 9/2004 | Lin |
| 6,796,984 B2 | 9/2004 | Soubeiran |
| 6,835,205 B2 | 12/2004 | Atkinson |
| 6,843,791 B2 | 1/2005 | Serhan |
| 6,896,677 B1 | 5/2005 | Lin |
| 6,905,500 B2 | 6/2005 | Jeon |
| 6,918,911 B2 | 7/2005 | Biedermann |
| 6,966,910 B2 | 11/2005 | Ritland |
| 6,986,771 B2 | 1/2006 | Paul |
| 6,989,011 B2 | 1/2006 | Paul |
| 6,997,927 B2 | 2/2006 | Jackson |
| 7,018,378 B2 | 3/2006 | Biedermann |
| 7,022,122 B2 | 4/2006 | Amrein |
| 7,029,475 B2 | 4/2006 | Panjabi |
| 7,125,410 B2 | 10/2006 | Freudiger |
| 7,137,985 B2 | 11/2006 | Jahng |
| 7,156,850 B2 | 1/2007 | Kim |
| 7,175,622 B2 | 2/2007 | Farris |
| 7,179,261 B2 | 2/2007 | Sicvol |
| 7,204,838 B2 | 4/2007 | Jackson |
| 7,211,086 B2 | 5/2007 | Biedermann |
| 7,261,714 B2 | 8/2007 | Richelsoph |
| 7,326,210 B2 | 2/2008 | Jahng |
| 7,329,258 B2 | 2/2008 | Studer |
| 7,335,200 B2 | 2/2008 | Carli |
| 7,419,714 B1 | 9/2008 | Magerl |
| 7,553,320 B2 | 6/2009 | Molz |
| 7,556,639 B2 | 7/2009 | Rothman |
| 7,621,912 B2 | 11/2009 | Harms |
| 7,621,940 B2 | 11/2009 | Harms |
| 7,632,292 B2 | 12/2009 | Sengupta |
| 7,641,673 B2 | 1/2010 | Le Couedic |
| 7,651,515 B2 | 1/2010 | Mack |
| 7,713,287 B2 | 5/2010 | Timm |
| 7,717,941 B2 | 5/2010 | Petit |
| 7,722,649 B2 | 5/2010 | Biedermann |
| 7,727,258 B2 | 6/2010 | Graf |
| 7,763,052 B2 | 7/2010 | Jahng |
| 7,776,071 B2 | 8/2010 | Fortin |
| 7,776,075 B2 | 8/2010 | Bruneau |
| 7,811,309 B2 | 10/2010 | Timm |
| 7,815,665 B2 | 10/2010 | Jahng |
| 7,833,256 B2 | 11/2010 | Biedermann |
| 7,846,187 B2 | 12/2010 | Jackson |
| 7,862,586 B2 | 1/2011 | Malek |
| 7,942,907 B2 | 5/2011 | Richelsoph |
| 7,988,710 B2 | 8/2011 | Jahng |
| 7,993,370 B2 | 8/2011 | Jahng |
| 8,012,178 B2 | 9/2011 | Hartmann |
| 8,157,843 B2 | 4/2012 | Biedermann |
| 8,221,467 B2 | 7/2012 | Butler |
| 8,241,362 B2 | 8/2012 | Voorhies |
| 8,974,497 B2 * | 3/2015 | Cho et al. ........................ 606/255 |
| 2002/0058942 A1 | 5/2002 | Biedermann |
| 2002/0072751 A1 | 6/2002 | Jackson |
| 2002/0082602 A1 | 6/2002 | Biedermann |
| 2002/0133155 A1 | 9/2002 | Ferree |
| 2002/0133159 A1 | 9/2002 | Jackson |
| 2003/0009226 A1 | 1/2003 | Graf |
| 2003/0041441 A1 | 3/2003 | Lin |
| 2003/0055426 A1 | 3/2003 | Carbone |
| 2003/0055427 A1 | 3/2003 | Graf |
| 2003/0083657 A1 | 5/2003 | Drewry |
| 2003/0100896 A1 | 5/2003 | Biedermann |
| 2003/0109880 A1 | 6/2003 | Shirado |
| 2003/0125741 A1 | 7/2003 | Biedermann |
| 2003/0149431 A1 | 8/2003 | Varieur |
| 2003/0153912 A1 | 8/2003 | Graf |
| 2003/0171749 A1 | 9/2003 | Le Couedic |
| 2003/0191470 A1 | 10/2003 | Ritland |
| 2003/0220642 A1 | 11/2003 | Freudiger |
| 2003/0220643 A1 | 11/2003 | Ferree |
| 2004/0002708 A1 | 1/2004 | Ritland |

(56) References Cited

U.S. PATENT DOCUMENTS

| | | | | |
|---|---|---|---|---|
| 2004/0049189 | A1 | 3/2004 | Le Couedic | |
| 2004/0049190 | A1 | 3/2004 | Biedermann | |
| 2004/0068258 | A1 | 4/2004 | Schlapfer | |
| 2004/0073215 | A1 | 4/2004 | Carli | |
| 2004/0097926 | A1 | 5/2004 | Kim | |
| 2004/0097933 | A1 | 5/2004 | Lourdel | |
| 2004/0106921 | A1 | 6/2004 | Cheung | |
| 2004/0116927 | A1 | 6/2004 | Graf | |
| 2004/0143264 | A1 | 7/2004 | McAfee | |
| 2004/0167523 | A1 | 8/2004 | Jackson | |
| 2004/0186474 | A1 | 9/2004 | Matthis | |
| 2004/0186478 | A1 | 9/2004 | Jackson | |
| 2004/0215191 | A1* | 10/2004 | Kitchen | 606/61 |
| 2004/0215192 | A1 | 10/2004 | Justis | |
| 2004/0225289 | A1* | 11/2004 | Biedermann et al. | 606/61 |
| 2004/0230191 | A1 | 11/2004 | Frey | |
| 2004/0230192 | A1 | 11/2004 | Graf | |
| 2004/0236327 | A1 | 11/2004 | Paul | |
| 2004/0236328 | A1 | 11/2004 | Paul | |
| 2004/0236329 | A1 | 11/2004 | Panjabi | |
| 2004/0260284 | A1 | 12/2004 | Parker | |
| 2004/0264386 | A1 | 12/2004 | Ha | |
| 2004/0267260 | A1 | 12/2004 | Mack | |
| 2005/0027292 | A1 | 2/2005 | Bernard | |
| 2005/0033295 | A1 | 2/2005 | Wisnewski | |
| 2005/0038432 | A1 | 2/2005 | Shaolian | |
| 2005/0049708 | A1 | 3/2005 | Atkinson | |
| 2005/0056979 | A1 | 3/2005 | Studer | |
| 2005/0065514 | A1 | 3/2005 | Studer | |
| 2005/0065516 | A1 | 3/2005 | Jahng | |
| 2005/0080414 | A1 | 4/2005 | Keyer | |
| 2005/0085814 | A1 | 4/2005 | Sherman | |
| 2005/0085815 | A1 | 4/2005 | Harms | |
| 2005/0113927 | A1 | 5/2005 | Malek | |
| 2005/0124991 | A1 | 6/2005 | Jahng | |
| 2005/0129499 | A1 | 6/2005 | Morris | |
| 2005/0131407 | A1 | 6/2005 | Sicvol | |
| 2005/0131421 | A1 | 6/2005 | Anderson | |
| 2005/0131422 | A1 | 6/2005 | Anderson | |
| 2005/0143737 | A1 | 6/2005 | Pafford | |
| 2005/0143823 | A1 | 6/2005 | Boyd | |
| 2005/0149020 | A1 | 7/2005 | Jahng | |
| 2005/0154389 | A1 | 7/2005 | Selover | |
| 2005/0154390 | A1 | 7/2005 | Biedermann | |
| 2005/0165396 | A1 | 7/2005 | Fortin | |
| 2005/0171543 | A1 | 8/2005 | Timm | |
| 2005/0177156 | A1 | 8/2005 | Timm | |
| 2005/0177157 | A1 | 8/2005 | Jahng | |
| 2005/0177164 | A1 | 8/2005 | Walters | |
| 2005/0182400 | A1 | 8/2005 | White | |
| 2005/0182401 | A1 | 8/2005 | Timm | |
| 2005/0182409 | A1 | 8/2005 | Callahan | |
| 2005/0187549 | A1 | 8/2005 | Jackson | |
| 2005/0192589 | A1* | 9/2005 | Raymond et al. | 606/99 |
| 2005/0202519 | A1 | 9/2005 | Barthe | |
| 2005/0203511 | A1 | 9/2005 | Wilson-MacDonald | |
| 2005/0203513 | A1 | 9/2005 | Jahng | |
| 2005/0203514 | A1* | 9/2005 | Jahng et al. | 606/61 |
| 2005/0203516 | A1 | 9/2005 | Biedermann | |
| 2005/0203517 | A1 | 9/2005 | Jahng | |
| 2005/0203518 | A1 | 9/2005 | Biedermann | |
| 2005/0203519 | A1 | 9/2005 | Harms | |
| 2005/0215999 | A1 | 9/2005 | Birkmeyer | |
| 2005/0216003 | A1 | 9/2005 | Biedermann | |
| 2005/0222569 | A1 | 10/2005 | Panjabi | |
| 2005/0222659 | A1 | 10/2005 | Olsen | |
| 2005/0245930 | A1 | 11/2005 | Timm | |
| 2005/0261685 | A1 | 11/2005 | Fortin | |
| 2005/0261686 | A1* | 11/2005 | Paul | 606/61 |
| 2005/0267471 | A1 | 12/2005 | Biedermann | |
| 2005/0277919 | A1 | 12/2005 | Slivka | |
| 2005/0277922 | A1 | 12/2005 | Trieu | |
| 2005/0288670 | A1 | 12/2005 | Panjabi | |
| 2005/0288672 | A1 | 12/2005 | Ferree | |
| 2006/0009768 | A1 | 1/2006 | Ritland | |
| 2006/0014259 | A9 | 1/2006 | Burke | |
| 2006/0025767 | A1 | 2/2006 | Khalili | |
| 2006/0036240 | A1 | 2/2006 | Colleran | |
| 2006/0041259 | A1 | 2/2006 | Paul | |
| 2006/0064090 | A1 | 3/2006 | Park | |
| 2006/0084984 | A1 | 4/2006 | Kim | |
| 2006/0106380 | A1 | 5/2006 | Colleran | |
| 2006/0106381 | A1 | 5/2006 | Ferree | |
| 2006/0129147 | A1 | 6/2006 | Biedermann | |
| 2006/0142758 | A1 | 6/2006 | Petit | |
| 2006/0142760 | A1 | 6/2006 | McDonnell | |
| 2006/0149235 | A1 | 7/2006 | Jackson | |
| 2006/0149291 | A1 | 7/2006 | Selover | |
| 2006/0155279 | A1 | 7/2006 | Ogilvie | |
| 2006/0161152 | A1 | 7/2006 | Ensign | |
| 2006/0184171 | A1 | 8/2006 | Biedermann | |
| 2006/0189983 | A1 | 8/2006 | Fallin | |
| 2006/0189984 | A1 | 8/2006 | Fallin | |
| 2006/0195093 | A1 | 8/2006 | Jahng | |
| 2006/0201609 | A1 | 9/2006 | Edwin | |
| 2006/0212033 | A1 | 9/2006 | Rothman | |
| 2006/0229607 | A1 | 10/2006 | Brumfield | |
| 2006/0229608 | A1 | 10/2006 | Foster | |
| 2006/0229612 | A1 | 10/2006 | Rothman | |
| 2006/0240533 | A1 | 10/2006 | Sengupta | |
| 2006/0247632 | A1 | 11/2006 | Winslow | |
| 2006/0247637 | A1 | 11/2006 | Colleran | |
| 2006/0247638 | A1* | 11/2006 | Trieu et al. | 606/69 |
| 2006/0260483 | A1 | 11/2006 | Hartmann | |
| 2006/0264935 | A1 | 11/2006 | White | |
| 2006/0264937 | A1 | 11/2006 | White | |
| 2006/0265074 | A1 | 11/2006 | Krishna | |
| 2006/0282080 | A1 | 12/2006 | Albert | |
| 2007/0003598 | A1 | 1/2007 | Trieu | |
| 2007/0005063 | A1 | 1/2007 | Bruneau | |
| 2007/0016190 | A1 | 1/2007 | Martinez | |
| 2007/0016201 | A1 | 1/2007 | Freudiger | |
| 2007/0019808 | A1 | 1/2007 | Gonzalez | |
| 2007/0049937 | A1 | 3/2007 | Matthis | |
| 2007/0055241 | A1 | 3/2007 | Matthis | |
| 2007/0055244 | A1 | 3/2007 | Jackson | |
| 2007/0055247 | A1 | 3/2007 | Jahng | |
| 2007/0161992 | A1 | 7/2007 | Kwak | |
| 2007/0191832 | A1 | 8/2007 | Trieu | |
| 2007/0191841 | A1* | 8/2007 | Justis et al. | 606/61 |
| 2007/0198088 | A1 | 8/2007 | Biedermann | |
| 2007/0233064 | A1 | 10/2007 | Holt | |
| 2007/0233073 | A1* | 10/2007 | Wisnewski et al. | 606/61 |
| 2007/0233085 | A1 | 10/2007 | Biedermann | |
| 2007/0233097 | A1 | 10/2007 | Anderson | |
| 2007/0270814 | A1 | 11/2007 | Lim | |
| 2007/0270819 | A1* | 11/2007 | Justis et al. | 606/61 |
| 2007/0270838 | A1 | 11/2007 | Bruneau | |
| 2007/0270843 | A1 | 11/2007 | Matthis | |
| 2008/0021469 | A1* | 1/2008 | Holt | 606/61 |
| 2008/0033435 | A1 | 2/2008 | Studer | |
| 2008/0058809 | A1 | 3/2008 | Graf | |
| 2008/0140133 | A1 | 6/2008 | Allard | |
| 2008/0147122 | A1 | 6/2008 | Jackson | |
| 2008/0161853 | A1 | 7/2008 | Arnold | |
| 2008/0161863 | A1 | 7/2008 | Arnold | |
| 2008/0183213 | A1 | 7/2008 | Veldman | |
| 2008/0195105 | A1 | 8/2008 | Sidebotham | |
| 2008/0195153 | A1 | 8/2008 | Thompson | |
| 2008/0262552 | A1 | 10/2008 | Kim | |
| 2008/0312694 | A1 | 12/2008 | Peterman | |
| 2009/0005817 | A1 | 1/2009 | Friedrich | |
| 2009/0012562 | A1 | 1/2009 | Hestad | |
| 2009/0030464 | A1 | 1/2009 | Hestad | |
| 2009/0048631 | A1 | 2/2009 | Bhatnagar | |
| 2009/0062866 | A1 | 3/2009 | Jackson | |
| 2009/0099608 | A1 | 4/2009 | Szczesny | |
| 2009/0131981 | A1 | 5/2009 | White | |
| 2009/0163953 | A1 | 6/2009 | Biedermann | |
| 2009/0204155 | A1 | 8/2009 | Aschmann | |
| 2009/0234388 | A1 | 9/2009 | Patterson | |
| 2009/0251573 | A1 | 10/2009 | Toyoda | |
| 2009/0281573 | A1 | 11/2009 | Biedermann | |
| 2010/0042156 | A1 | 2/2010 | Harms | |

(56) References Cited

U.S. PATENT DOCUMENTS

| | | |
|---|---|---|
| 2010/0069962 A1 | 3/2010 | Harms |
| 2010/0069964 A1 | 3/2010 | Lechmann |
| 2010/0114169 A1 | 5/2010 | Le Couedic |
| 2010/0114173 A1 | 5/2010 | Le Couedic |
| 2010/0174317 A1 | 7/2010 | Timm |
| 2010/0204736 A1 | 8/2010 | Biedermann |
| 2011/0054534 A1 | 3/2011 | Biedermann |
| 2012/0265247 A1 | 10/2012 | Biedermann |
| 2014/0031868 A1 | 1/2014 | Biedermann |

FOREIGN PATENT DOCUMENTS

| | | |
|---|---|---|
| EP | 667127 | 8/1995 |
| EP | 677277 | 10/1995 |
| EP | 516567 | 7/1997 |
| EP | 669109 | 5/1999 |
| EP | 732081 | 5/2000 |
| EP | 1281364 | 1/2004 |
| EP | 1364622 | 7/2005 |
| EP | 1579816 | 9/2005 |
| EP | 1388323 | 1/2007 |
| EP | 1574173 | 1/2007 |
| EP | 1523949 | 6/2007 |
| EP | 1747760 | 10/2009 |
| EP | 1488751 | 11/2009 |
| EP | 1586276 | 11/2009 |
| EP | 1776927 | 9/2010 |
| EP | 1658815 | 3/2012 |
| FR | 2717370 | 9/1995 |
| GB | 2382307 | 5/2003 |
| JP | 2004073855 | 3/2004 |
| JP | 2005118569 | 5/2005 |
| WO | WO 9501132 | 1/1995 |
| WO | WO 9505783 | 3/1995 |
| WO | WO 9513755 | 5/1995 |
| WO | WO 9641582 | 12/1996 |
| WO | WO 0145576 | 6/2001 |
| WO | WO 0156489 | 8/2001 |
| WO | WO 0207622 | 1/2002 |
| WO | WO 0217803 | 4/2002 |
| WO | WO 0243603 | 6/2002 |
| WO | WO 02069854 | 9/2002 |
| WO | WO 03007828 | 1/2003 |
| WO | WO 03009737 | 2/2003 |
| WO | WO 03041441 | 5/2003 |
| WO | WO 03041599 | 5/2003 |
| WO | WO 03047441 | 6/2003 |
| WO | WO 02102259 | 12/2003 |
| WO | WO 2004024011 | 3/2004 |
| WO | WO 2004034916 | 4/2004 |
| WO | WO 2004064653 | 8/2004 |
| WO | WO 2005027761 | 3/2005 |
| WO | WO 2005030066 | 4/2005 |
| WO | WO 2005039454 | 7/2005 |
| WO | WO 2005013839 | 8/2005 |
| WO | WO 2005044117 | 8/2005 |
| WO | WO 2005094704 | 10/2005 |
| WO | WO 2005030031 | 1/2006 |
| WO | WO 2006066053 | 6/2006 |
| WO | WO 2006079531 | 8/2006 |
| WO | WO 2006118866 | 11/2006 |
| WO | WO 2006063107 | 12/2006 |
| WO | WO 2007007545 | 1/2007 |
| WO | WO 2006116437 | 2/2007 |
| WO | WO 2006115539 | 5/2007 |
| WO | WO 2008003047 | 6/2008 |

OTHER PUBLICATIONS

Betz, "Compairson of Anterior and Posterior Instrumentation for Correction of Adolsecent Thoracic Idiipathic Scoliosis", SPINE, Feb. 1, 1999, vol. 24, Issue 3, pp. 225-239.

Desroches "Biomechanical modeling of anterior spine instrumentation in AIS", Stud Health Technol Inform, 2006, vol. 123, pp. 415-418—abstract.

Hefti, "Repair of lumbar spondylolysis with a hook-screw", Int Orthop., 1992, vol. 16, Issue 1, pp. 81-85—abstract.

Nohara, "Biomechanical study of adjacent intervertebral motion after lumbar spinal fusion and flexible stabilization using polyethylene-terephthalate bands", J Spinal Discord Tech, Jun. 2004, vol. 17, Issue 3, pp. 215-219—abstract.

Poulin, "Biomechanical modeling of instrumentation for the scoliotic spine using flexible elements:a feasibility study", Ann Chir, 1998, 52(8), pp. 761-767—abstract.

Sanders, "A Preliminary Investigation of Shape Memory Alloys in the Surgical Correction of Scoliosis", SPINE, Sep. 15, 1993, vol. 18, Issue 12, pp. 1640-1646.

Smith, "Does Instrumented Anterior Scoliosis Surgery Lead to Pyphosis, Pseudarthrosis, or Inadequate Correction in Adults", SPINE, Mar. 1, 2002, vol. 27, Issue 5, pp. 529-534.

Teitelbaum, "New Percutaneously Inserted Spinal Fixation System", SPINE, Mar. 11, 2004, vol. 29, Issue 6, pp. 703-709.

Veldhuizen, "A Scoliosis Correction Device Based on Memory Metal", Med. Eng. Phys., 1997, vol. 19, pp. 171-179, Elsevier Science Ltd.

* cited by examiner

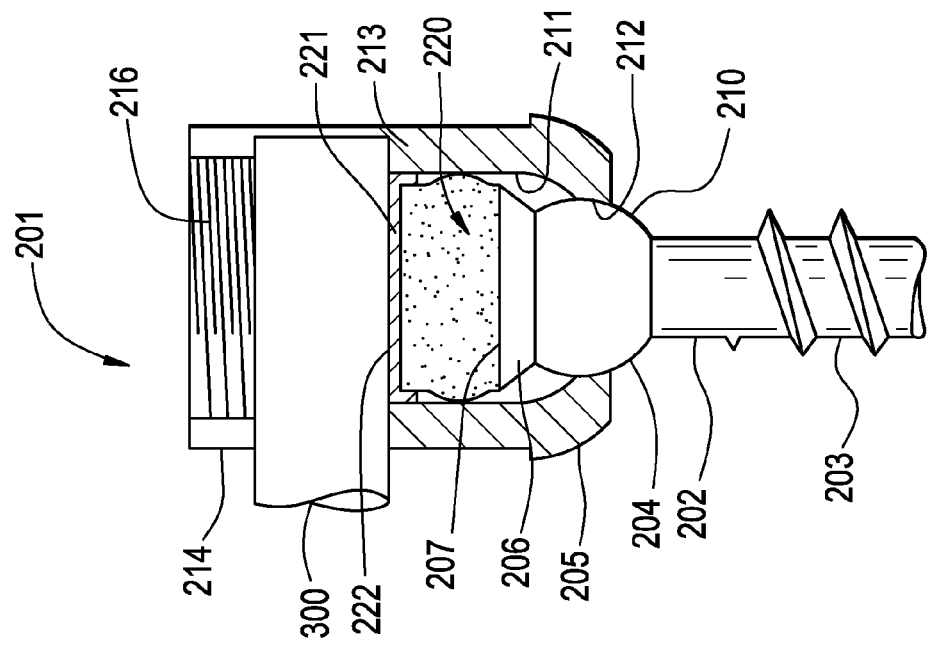
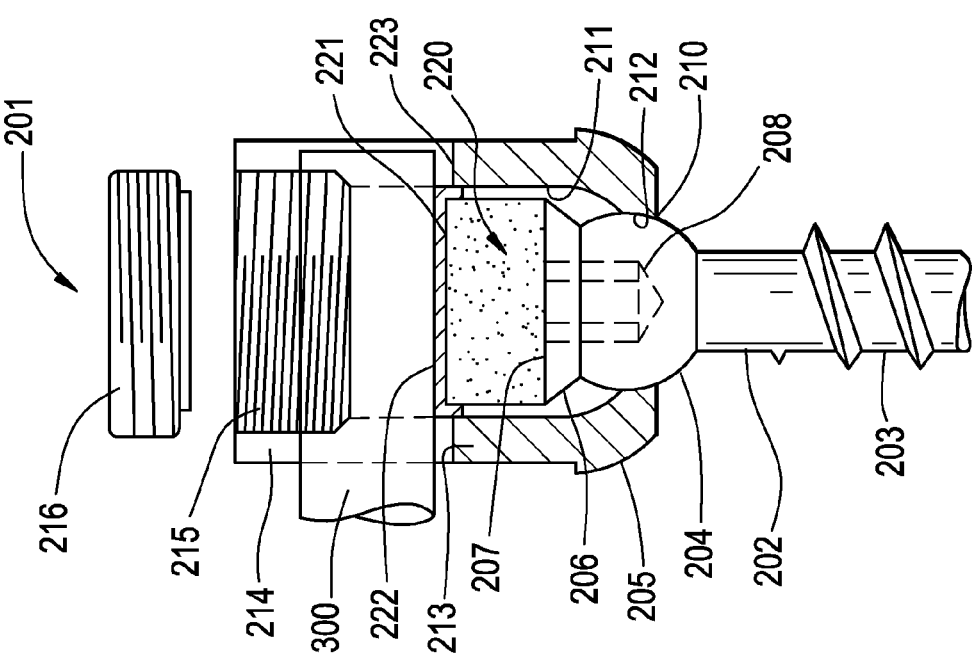

POLYMERIC PEDICLE RODS AND METHODS OF MANUFACTURING

CONTINUING DATA

This patent application claims priority from co-pending U.S. Provisional Application Ser. No. 61/014,851, filed Dec. 19, 2007, entitled "Polymeric Pedicle Rods and Methods of Manufacturing, (Attorney Docket No. DEP6072USPSP).

BACKGROUND OF THE INVENTION

Metallic-based pedicle rod and screw systems are often used in spinal surgeries to correct spinal deformities and intervertebral disc degeneration. Although these systems have been shown to be useful, there has nonetheless been documentation of a number of clinical problems with these systems. First, there are reports of pedicle screw loosening due to a material stiffness that is significantly higher than that of bone. There are reports of reduced postoperative visualization due to artifacts incurred with radio-imaging of the metallic components. Low interbody fusion rates are thought to be due to excessive load transfer through the posterior column, again due to a material stiffness that is significantly higher than that of bone. Lastly, adjacent level hypermotion, excessive loading and physiological breakdown are also thought to be due to the use of metallic rods.

In response to these issues, spinal device companies have recently launched polyetheretherketone (PEEK) polymer rod systems in an attempt to minimize the imaging scatter associated with metallic implants and to increase anterior load sharing at the operative level. Spinal companies have also developed posterior pedicle-based motion systems in attempt to address these clinical problems as well.

U.S. Pat. No. 4,743,260 discloses polymeric pedicle rods, and teaches the use of polymers with carbon fiber reinforcements to enhance strength. In addition, a 1995 thesis compiled by Balli at the University of Akron specifically discloses the use of chopped carbon fiber reinforced PEEK for pedicle-based spinal fixation systems.

PCT Patent Publication WO2006/118866 (Trieu) discloses composite components for use in spinal fixation systems, wherein the composite components comprise polyetheretherketone (PEEK) or another non-resorbable or resorbable polymeric material and at least one metal. Incorporation of PEEK or another non-resorbable or resorbable polymeric material into the components allows average or mean physical properties (e.g., tensile strength, modulus of elasticity, etc.) of the components to be modulated. The composition and orientation of the composite components can be advantageously chosen to produce components with desired physical characteristics.

US Published Patent Application 2006/0229607 (Brumfield) discloses a system, kit and method for treatment of the spinal column, including a plurality of elongate support elements configured for placement across multiple levels of the spinal column wherein at least one of the elongate support elements is formed of a first material and at least one other of the elongate support elements is formed of a second material different from the first material, with the first material having a modulus of elasticity that is different from that of the second material. A plurality of fixation elements are provided which are configured to engage a number of the elongate support elements to the spinal column and which are formed of a third material that is bio-compatible with each of the first and second materials. Further disclosed is an operative kit with elongate support elements (Pedicle rods) with two or more materials, i.e. a kit having metallic and polymeric rods.

Other patents and published patent applications related to this subject matter include: US 2004/0225289 (Biedermann I); US2005/0154390 (Biedermann II); European patent Publication 1579816 (Biedermann III); US 2005/0143823 (Boyd); US2005/0182409 (Callahan); US 2004/0236329 (Panjabi I); US 2005/0222569 (Panjabi II); US 2004/0236327 (Paul I); US 2004/0236328 (Paul II); US2005/0171543 (Timm I); US 2005/0182401 (Timm II); US 2005/0177164 (Walters); and US 2005/0182400 (White).

SUMMARY OF THE INVENTION

The present invention involves innovative devices and methods of manufacture of spinal stabilization systems with posterior pedicle rods and pedicle screws. These devices utilize a rod having an internally reinforced polymeric core that is at least partially encased within at least one polymeric coating. The preferred embodiment utilizes a Carbon Fiber-Reinforced PEEK (CFRP) core that is at least partially encased within at least one polymeric coating. The diameter and geometry of the central core and external rod profile can be designed to adjust stiffness in various planes of motion. The core or external rod profile can include ribs to increase support in various planes. The number of carbon fiber layers, the percentage of carbon fiber, and the diameter, construction and planes of fiber orientation can, via various methods of manufacture, be adjusted to further customize rod stiffness in varying planes. These devices can be further grouped into a family and provided as a kit, allowing intra-operative flexibility to select the desired geometry and level of posterior stiffness/constraint supplementation.

Therefore, in accordance with the present invention, there is provided a spinal pedicle rod comprising an internally reinforced polymeric core that is at least partially encased within a polymeric coating.

Also in accordance with the present invention, there is provided a spinal assembly comprising:
  a. a spinal pedicle rod comprising an internally reinforced polymeric core that is at least partially encased within at least one polymeric coating, and
  b. a bone anchor having a recess for accepting the rod, wherein the rod is fixed in the recess of the bone anchor.

Also in accordance with the present invention, there is provided a spinal pedicle rod comprising a core comprising continuous carbon fiber, wherein the core is at least partially encased within a polymeric coating.

The concepts of the present invention differ from prior art as they:
  disclose specific PEEK-coated CFRP pedicle rod designs that enhance fatigue endurance and minimize wear at the set screw/rod interface;
  employ specific manufacturing methods to orient the reinforcement fibers in desired directions and coat the core with neat PEEK;
  disclose embodiments that utilize continuous fiber internal reinforcement;
  disclose specific geometries of fiber orientation that balance stiffness and strength in various planes of motion and fatigue endurance; and
  utilize the CFRP core for MIS inserter attachment.

DESCRIPTION OF THE FIGURES

FIG. 4b discloses a longitudinal cross-section of the pultruded core of FIG. 4a

FIG. 4c discloses an axial cross-section of FIG. 4a.

FIG. 5b discloses a longitudinal cross-section of the core of FIG. 5a.

FIG. 6b discloses a longitudinal view of the core of FIG. 6a.

FIG. 6c discloses an axial cross section of FIG. 6a.

FIG. 21 shows an illustration in partial section of an embodiment of the anchoring device in the unloaded state.

FIG. 22 shows an illustration in partial section of the anchoring device according to FIG. 21 in the loaded state in the resting position.

DETAILED DESCRIPTION OF THE INVENTION

Figure 1A:
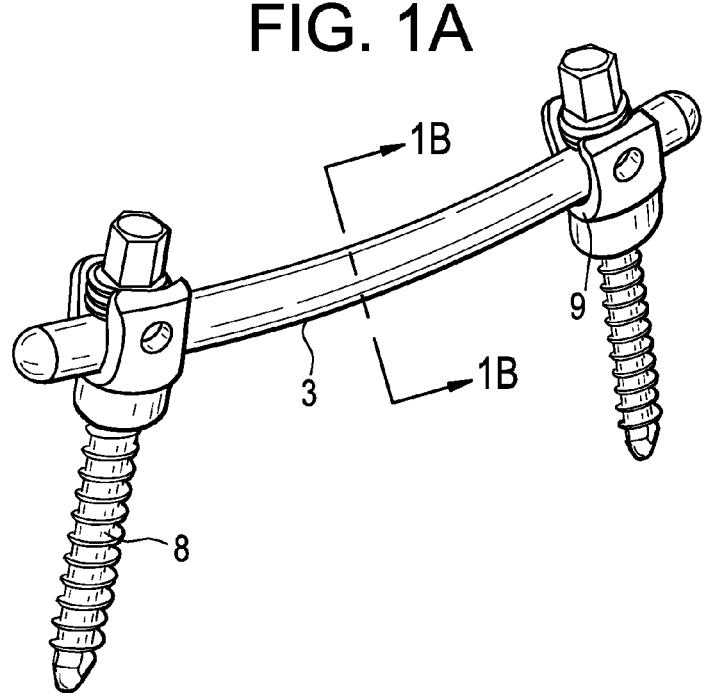
FIG. 1a discloses a perspective view of a spinal assembly of the present invention.
Figure 1B:
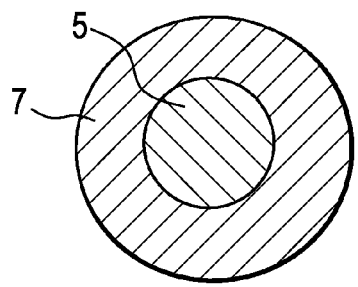
FIGS. 1b-c discloses axial cross-sections of the rod of FIG. 1a, wherein the rod has an internally reinforced polymeric core that is encased within a polymeric coating.
Figure 1C:
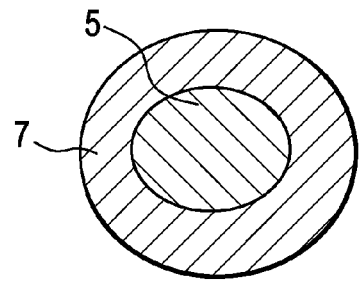

Now referring to FIGS. 1a-c, there are provided devices utilizing an internally reinforced polymeric core that is at least partially encased within at least one polymeric coating. In particular, there is a spinal fixation assembly 1 comprising:
a) a spinal pedicle rod 3 comprising an internally reinforced polymeric core 5 that is at least partially encased within at least one polymeric coating 7, and
b) a bone anchor 8 having a recess 9 for accepting the rod, wherein the rod is fixed in the recess of the bone anchor.

FIG. 1a also shows that the rod may be bent (pre-lordosed) in order to accommodate the curvature of the spine in the region of interest. FIGS. 1b-c disclose axial cross-sections of the rod of FIG. 1a, wherein the rod has an internally reinforced polymeric core 5 that is encased within a polymeric coating 7. Whereas FIG. 1b discloses a circular cross-section, FIG. 1c discloses an oval cross-section. Non-circular cross-sections will provide better stiffness in certain planes in torsion and/or flexion-extension.

Figure 2A:
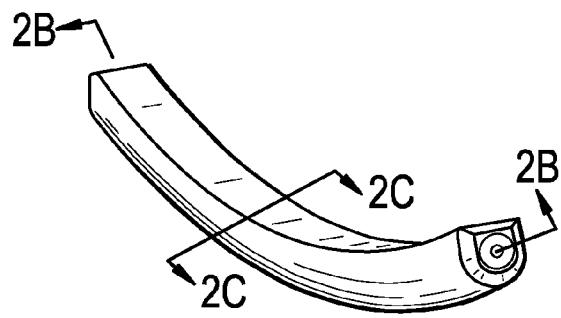
FIGS. 2a-d disclose various views of a rod utilizing a carbon fiber reinforced PEEK (CFRP) core that is at least partially encased within at least one polymeric coating, wherein the diameter and geometry of the central core and external rod profile are designed to adjust stiffness in various planes of motion.
Figure 2B:
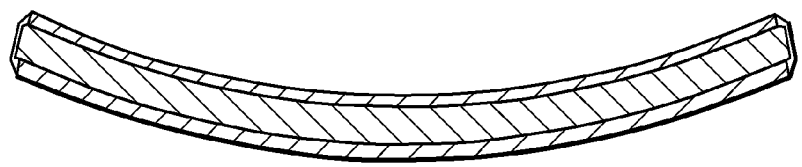
Figure 2C:
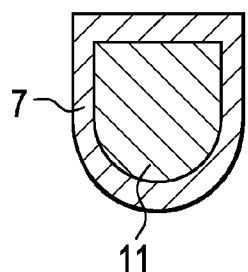
Figure 2D:
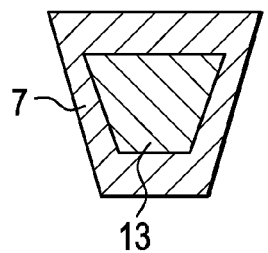

Now referring to FIGS. 2a-b, there are provided preferred embodiments of the rod utilizing a carbon fiber reinforced PEEK (CFRP) core that is at least partially encased within at least one polymeric coating, wherein the diameter and geometry of the central core and external rod profile can be designed to adjust their stiffnesses in various planes of motion. In some embodiments, the core has a non-circular axial cross-section. In some embodiments, the axial cross-section has a height and a width, wherein the height is greater than the width. In particular, FIG. 2c discloses a core 11 having a semi-oval axial cross-section. It is believed that the semi-oval shape of the core will desirably increase the stiffness of the rod in the flexion/extension plane. In other embodiments, such as in FIG. 2d, the core 13 has a frustoconical axial cross-section. It is believed that the frustoconical shape of the core will impart the desirable property of increased stiffness in a desired plane (flexion/extension shown) to the rod. In these embodiments, the shape of the coating 7 mimics the cross-section of the core.

Figure 3A:
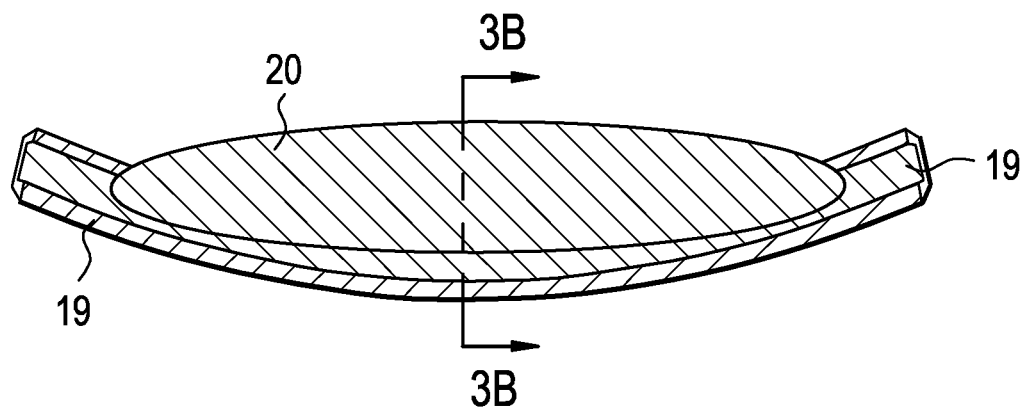
FIGS. 3a-b disclose respective saggital and axial cross-sectional views of a rod wherein the core or external rod profile includes a plurality of ribs to increase support in various planes.
Figure 3B:
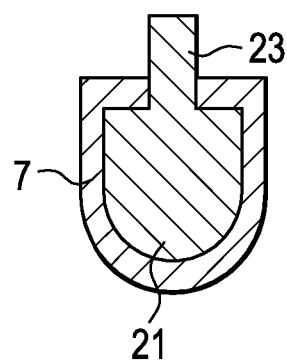

Now referring to FIGS. 3a-b, there are provided rods wherein the core or external rod profile can include ribs to increase support in various planes. In particular, FIGS. 3a-b disclose a rod having a pair of end portions 19, and an intermediate section 20 therebetween, wherein the core of the intermediate section has a base section 21 and a rib 23 extending from the base section. It is believed that the rib of FIG. 3a-b will desirably increase the stiffness of the rod in the flexion/extension plane. FIG. 3b also discloses outer coating 7.

Now referring to FIGS. 4a-5d, there are provided rods wherein the number of carbon fiber layers, the percentage of carbon fiber, diameter(s), construction and planes of fiber orientation is adjusted, via various methods of manufacture, to further customize rod stiffness in varying planes.

Figure 4A:
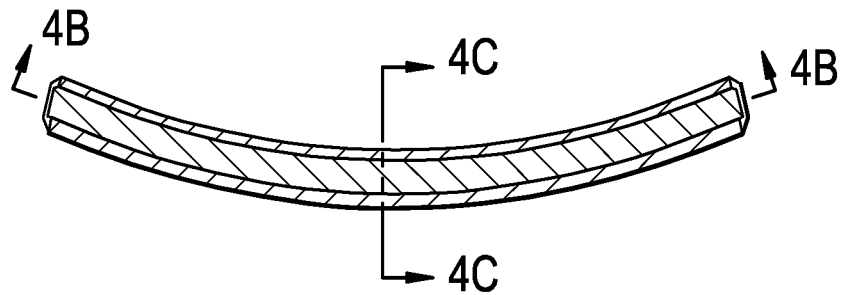
FIG. 4a discloses a rod having a pultruded core.
Figure 4B:
Figure 4C:
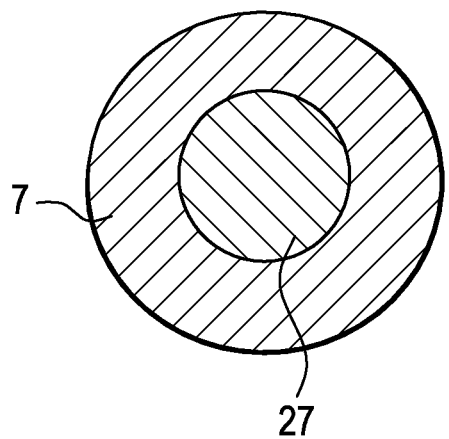

In particular, FIG. 4a discloses a rod having a pultruded core. Continuous carbon fiber is impregnated with PEEK and pulled through an extruder, thereby producing the pultruded core. Pull-off speed, fiber geometry, fiber bundle numbers and orientation are adjusted to optimize tensile, flexural and compressive endurance. Hence, as shown in FIG. 4b (which discloses only the core), the carbon fibers 25 align themselves within the core 27 along the longitudinal axis of the rod. FIG. 4c shows an axial cross-section of the entire rod. It is believed that this embodiment in FIGS. 4a-c has the advantage of increased flexural stiffness, thereby allowing for a reduced cross-section and rod size that provides a flexural stiffness substantially equivalent to a solid PEEK device of similar size. FIG. 4c also discloses outer coating 7.

Figure 5A:
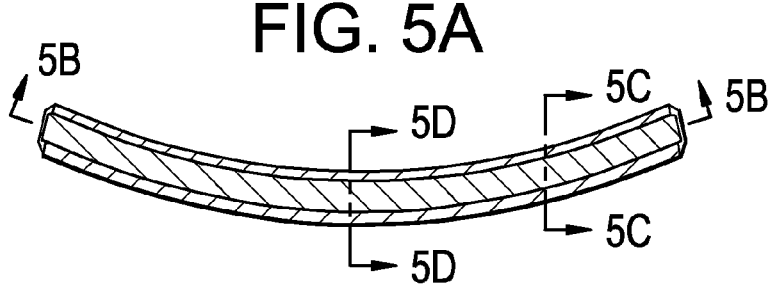
FIG. 5a discloses a rod having a carbon fiber core that varies over the length of the rod.
Figure 5B:
Figure 5C:
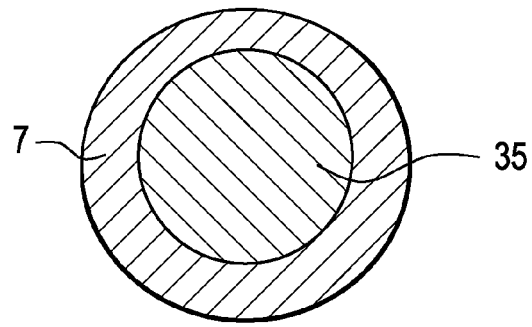
FIG. 5c discloses an axial cross-section of a pultruded core taken in the intermediate section of the rod.
Figure 5D:
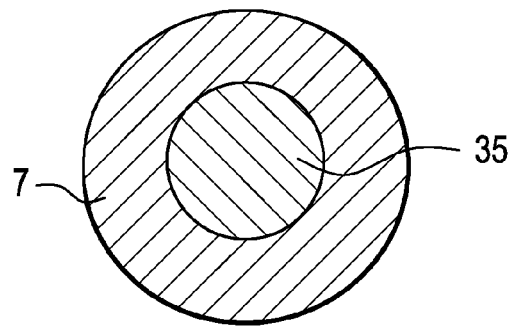
FIG. 5d discloses an axial cross-section of a pultruded core taken in an endportion of the rod.

FIG. 5a discloses a rod having a variable carbon fiber core. In particular, as shown in FIG. 5b (which discloses the core only), the core of this rod has a pair of end portions 31, and an intermediate section therebetween 35, wherein the intermediate section has a high packing density of continuous carbon fiber and the end portions have a low packing density of continuous carbon fiber. Also, as shown in FIG. 5b, the carbon fibers 25 throughout the core align themselves along the longitudinal axis of the rod. FIG. 5c discloses an axial cross-section of the pultruded core taken in the intermediate section of the rod, while FIG. 5d discloses an axial cross-section of the pultruded core taken in an endportion of the rod. It is believed that this embodiment in FIG. 5a-d has the advantage of providing customizable flexural and compressive stiffness at desired locations. FIGS. 5c-d also disclose outer coating 7.

Figure 6A:
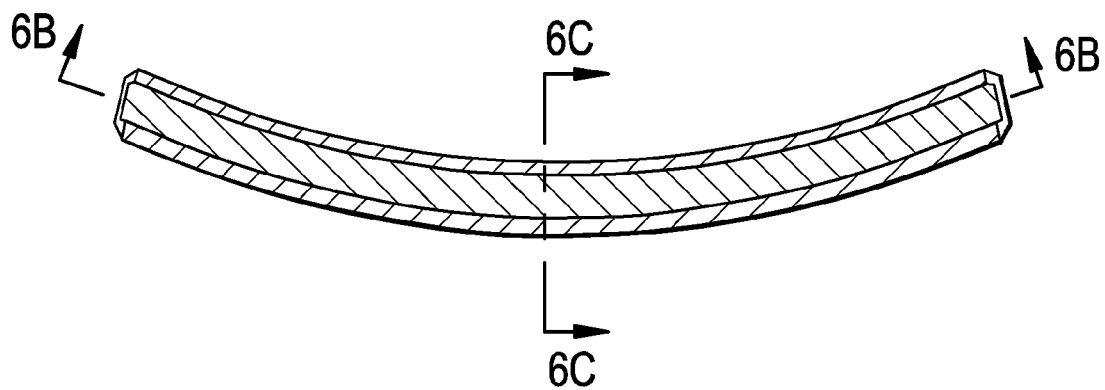
FIG. 6a discloses a rod having a CFRP core having continuous fibers, wherein a helical portion of the core is made by filament winding.
Figure 6B:
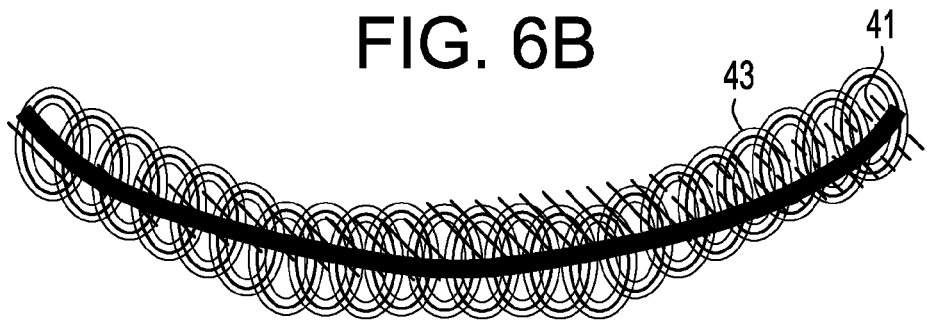
Figure 6C:
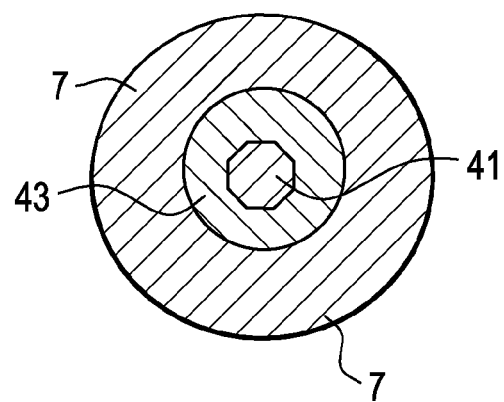

Now referring to FIG. 6a, there is provided a rod having a CFRP core having continuous fibers, wherein the core is made by filament winding. A continuous carbon fiber mandrel is concentrically wrapped with continuous carbon fiber that has been impregnated with base resin (PEEK). Thus, as shown in FIG. 6b, the core of the rod comprises i) a continuous carbon fiber center 41 extending along the longitudinal axis of the core, and ii) a filament 43 wrapped in a helical manner around the continuous carbon fiber center, wherein the filament comprises carbon fibers loaded in a polymer matrix. Preferably, the carbon fibers loaded in the polymer matrix are chopped. FIG. 6c shows an axial cross-section of FIG. 6a. It is believed that this embodiment in FIG. 6a-c has the advantage of providing increased compressive and flexural stiffness for a given cross-sectional area when compared to PEEK or CFRP. FIG. 6c also discloses outer coating 7.

Figure 7A:
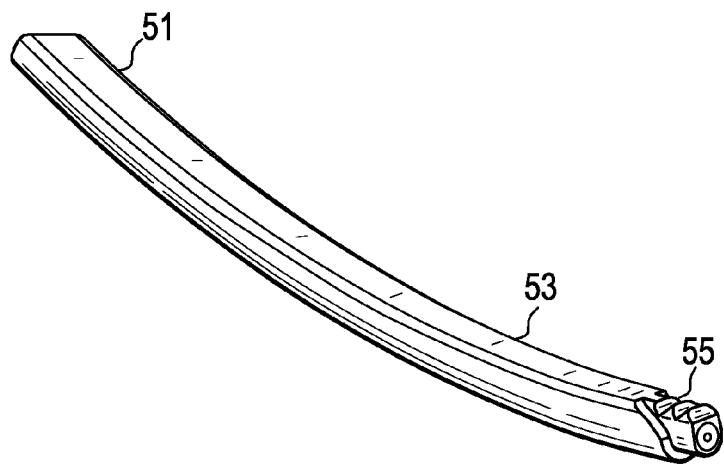
FIGS. 7a-c disclose various views of a polymeric pedicle rod including features for MIS insertion.
Figure 7B:
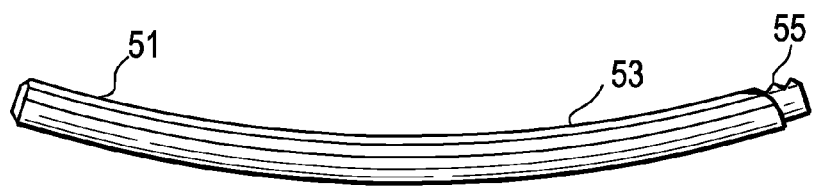
Figure 7C:
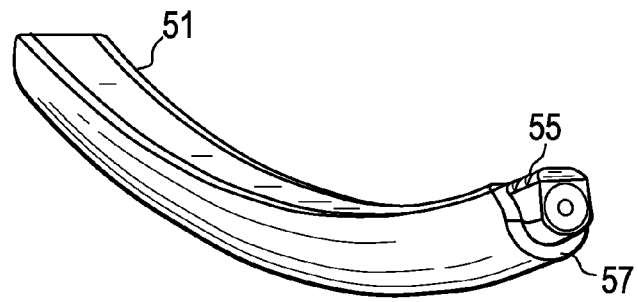

Now referring to FIGS. 7a-c, there is provided a polymeric pedicle rod including features for insertion during minimally invasive surgery (MIS). These features can be on the outer coating 57, although in the preferred embodiment the features are on continuous carbon fiber core, as the core provides increased strength, stiffness, and resistance to damage upon insertion. In this particular set of FIGS. 7a-c, the rod has a pair of end portions 51, and an intermediate section 53 therebetween, and an MIS insertion feature including at least one notch 55 (for example, a plurality of notches) perpendicular to the longitudinal axis. In other embodiments, the MIS insertion feature is a tapered end portion.

In some embodiments, the CFRP core of the present invention is manufactured with the carbon fibers either in the form of chopped carbon fibers or in the form of continuous carbon fibers.

When chopped carbon fibers are selected to be in the core, carbon fiber segments of consistent or variable diameters and lengths are blended into the PEEK resin formed into pedicle rods. This process can include either direct machining from CFRP extruded rod stock or molded form, or net shape compression or injection molding of blended CFRP resin. The orientation of the fibers can be generally aligned into the loaded direction.

Continuous carbon fibers increase the fabricated form stiffness in the plane of fiber orientation. The continuous carbon fibers are generally oriented in the axial plane of the device, thereby increasing the compressive strength of the spinal construct. When continuous carbon fibers are selected to be in the core, the continuous carbon fibers can be multiple strands, braids, bundles, or weaved forms including sheets. The continuous carbon fibers can be coated and impregnated with PEEK and fabricated into pedicle rods via methods such as hot pressing, filament winding and pultrusion.

When hot pressing is selected, continuous carbon fibers are heat pressed with PEEK into a machining blank or a net rod form.

When filament winding is selected, a continuous carbon fiber mandrel is concentrically wrapped with continuous carbon fiber that has been impregnated with base resin (PEEK). Manufacturing variables such as wrapping geometry, fiber bundle number and orientation may be adjusted to optimize tensile, flexural and compressive endurance. Either blanks or net shape forms can be produced.

When pultrusion is selected, continuous carbon fiber is impregnated with PEEK and pulled through an extruder. Manufacturing variables such as pull-off speed, fiber geometry, fiber bundle numbers and orientation are adjusted to optimize tensile, flexural and compressive endurance. Added fiber orientation and external rod lordotic shape can be varied via take-off rolls or subsequent heat bending.

Broadly, any non-resorbable, biocompatible polymer may be used as the neat coating of the present invention. In preferred embodiments, the carbon fiber/polymer matrix core is coated with a PEEK coating. The polymer coating prevents direct set screw contact upon the core, thereby minimizing carbon fiber wear in the rod during use. The polymer coating thickness can range from microns to millimeters. This thickness also provides a substrate for set screw impingement and/or compression into the rod, thereby enhancing attachment as well as providing a container to capture any debris that maybe formed at the inner boundaries of the core. Coating attachment can be increased by surface modifications to or pretreatment of the core, including surface machining, blasting, chemical/laser etching, dipping, priming, adhesive applications, and inclusion of surface features such as dovetails and undercut rings.

In some embodiments, the coating is applied by hot pressing, wherein the carbon fiber core can be coated with direct compression or roll coating under thermal exposure. In some embodiments, the coating is applied by sputtering or hot spray coating, wherein a spray of molten PEEK can coat the carbon fiber core. In some embodiments, the coating is applied by overmolding, wherein the carbon fiber core is overmolded with PEEK resin with or without core centralization features. In some embodiments, the coating is applied by coextrusion, wherein a continuous carbon fiber/polymer matrix core is co-extruded with a coating of PEEK. In some embodiments, the coating is applied by inner-molding (Filled PEEK Sleeve), wherein a tubular form of PEEK is injected with CFRP or continuous carbon fiber PEEK via standard injection or Continuous Flow Molding (CFM).

In preferred embodiments, radiographic markers can be added to the rods of the present invention. This can be accomplished by press fitting, heat staking, adhesives, overmolding of radiopaque items (tantalum or titanium beads, rods, or fibers) into the ends of the rods, or metallic threads that are fabricated with or weaved within the CFRP core. Alternative means of providing radiopaque markers also include printing a radiopaque medium onto a polymer surface. The polymer can be loaded with non-metallic, radiopaque fillers such as barium sulfate, calcium sulfate and zirconia.

In addition, metallic set screws are typically used to fix the rods of the present invention into the recess of the screws of the assembly. These set screws can be fitted with a non-metallic insert or liner to avoid metal-to-polymer contact between the set screw and the rod of the present invention, hereby minimizing wear and slip potential, as well as minimizing rod damage from screw compression.

These components of the present invention may be made from any non-resorbable material appropriate for human surgical implantation, including but not limited to, surgically appropriate metals, and non-metallic materials, such as carbon fiber composites, polymers and ceramics. In particular, the spinal rods preferably have CFRP cores and polymer coatings. The bone anchors are generally made from metals and/or ceramics.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX delta™, available from CeramTec of Plochingen, Germany. Depending on the material chosen, a smooth surface coating may be provided thereon to improve performance and reduce particulate wear debris.

In some embodiments, the bone anchor consists essentially of a metallic material, preferably a titanium alloy or a chrome-cobalt alloy. In some embodiments, the bone anchor may be coated with a wear-resistant coating, such as diamond film, in order to reduce wear.

In some embodiments, the rod core is made from a composite comprising carbon fiber. Composites comprising carbon fiber are advantageous in that they typically have a strength and stiffness that is superior to neat polymer materials such as a polyarylethyl ketone PAEK. In some embodiments, the rod is made from a polymer composite such as a PEEK-carbon fiber composite.

Preferably, the composite comprising carbon fiber further comprises a polymer. Preferably, the polymer is a polyarylethyl ketone PAEK. More preferably, the PAEK is selected from the group consisting of polyetherether ketone PEEK, polyether ketone ketone PEKK and polyether ketone PEK. In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present as chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone PAEK, and
b) 1-60% (more preferably, 20-40 vol %) carbon fiber, wherein the polyarylethyl ketone PAEK is selected from the group consisting of polyetherether ketone PEEK, polyether ketone ketone PEKK and polyether ketone PEK.

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

The preferred embodiment of the rod employs a neat PEEK coating but alternate coatings including polyurethanes, UHMWPE, and ceramics can be utilized.

Although carbon fiber is currently the preferred reinforcement material of the present invention, other internal reinforcement materials known to industry may also be utilized (such as glass, PLT, KLVLAR™ (tradename?), clay, pararamid, self-reinforced polyphenylene, polysulfones, polyethersulfones, PMMA, DYNEEMA™, ultra high molecular weight polyethylene (UHMWPE), and talc).

In use, the reinforced polymeric rod is implanted in a similar manner to that known in the art of implantation of metallic rods and screw systems including open procedures and MIS insertion means.

The flexible rods of the present invention can also be used advantageously with mobile screw concepts. In some embodiments (shown in FIGS. 8, 19 and 20), the mobile screw includes a mobile bearing element disposed between the screw head and the rod, wherein the mobile element forms a ball and socket connection with the screw head. In other embodiments (as in FIGS. 21-23), the mobile screw uses a resilient pressure element acting on the head, wherein upon movement of the element from a first angular position of the shank relative to said receiving part into a second angular position, the pressure element exerts a return force onto the head to urge the element towards the first angular position.

Figure 8:
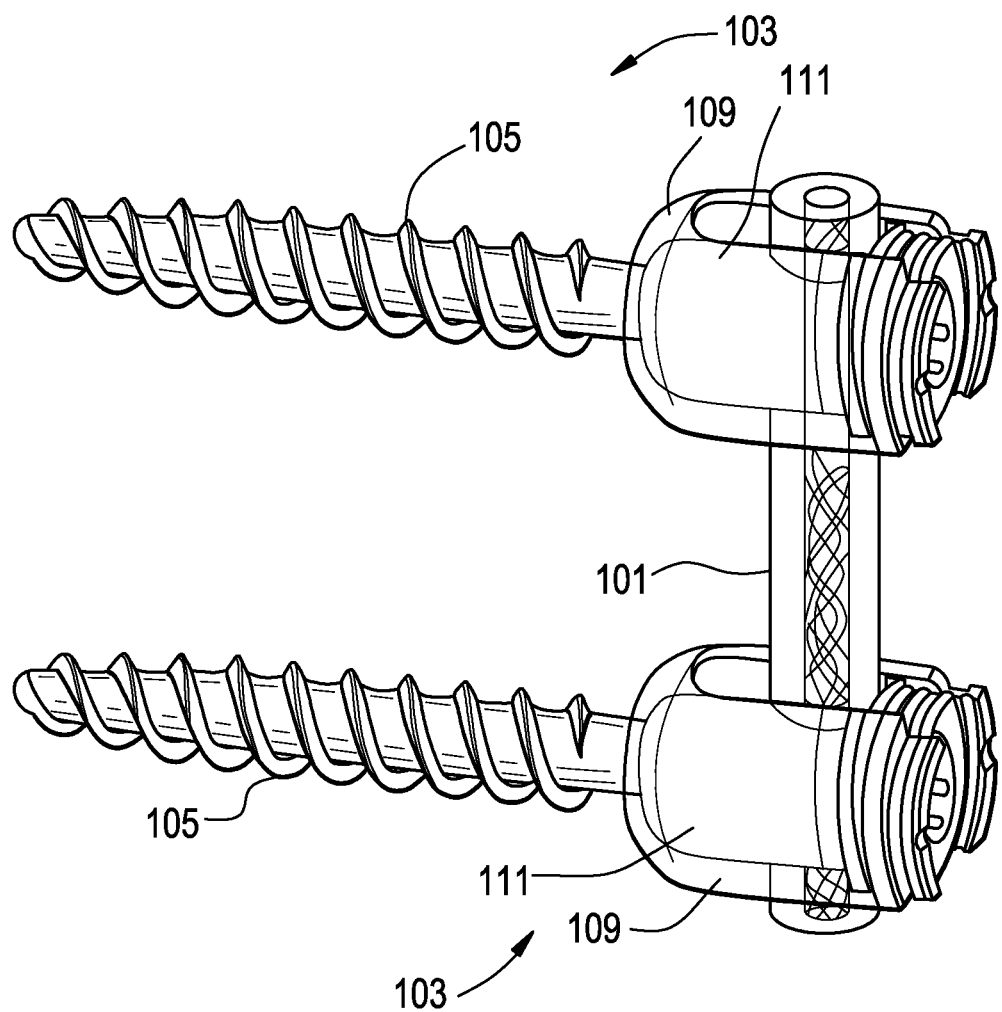
FIG. 8 discloses a flexible rod of the present invention combined with a pair of dynamic anchoring devices.
Figure 19:
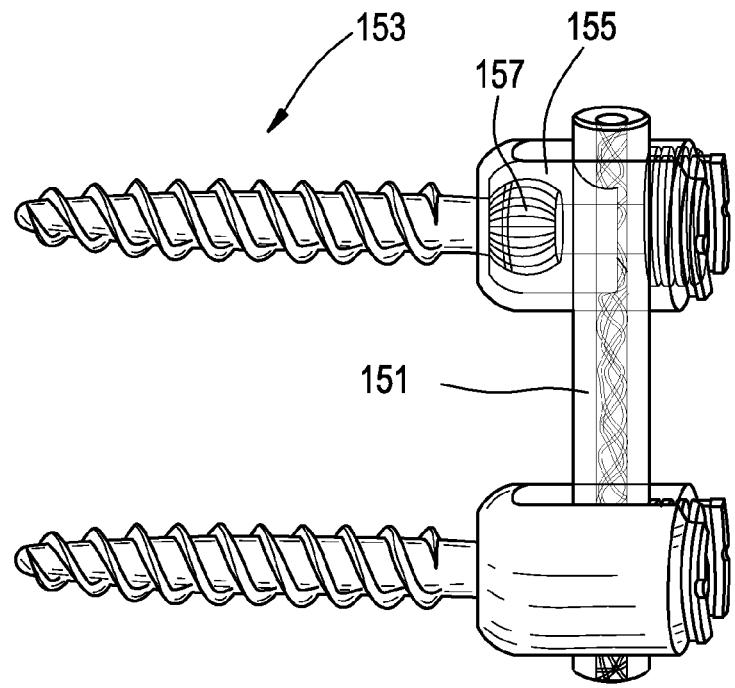
FIGS. 19 and 20 each discloses a flexible rod of the present invention combined with a pair of dynamic anchoring devices.
Figure 20:
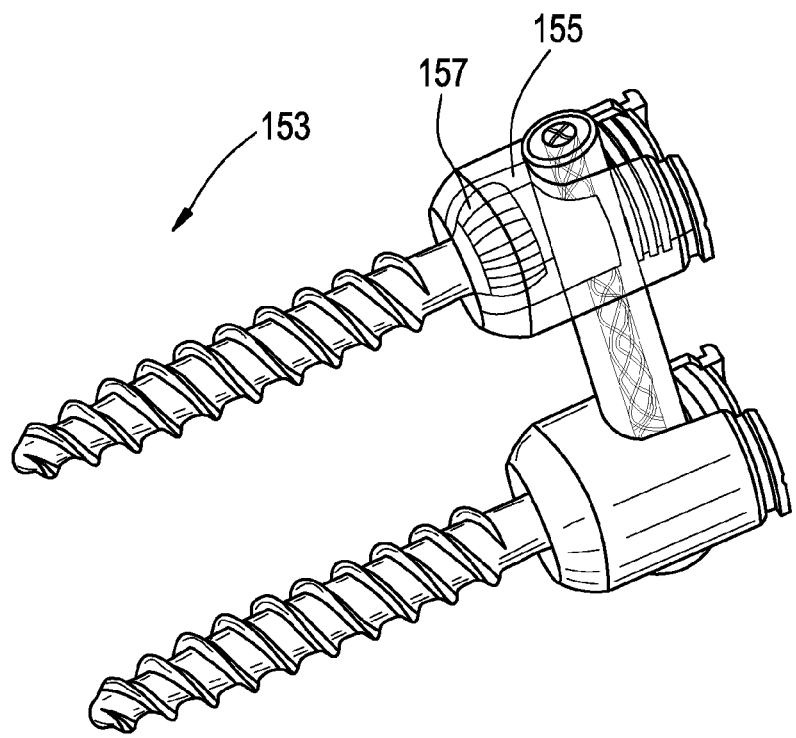

In the embodiments wherein the mobile screws use a mobile bearing element between the screw head and the rod (wherein the mobile element forms a ball and socket connection with the screw head), various embodiments of such a dynamic screw are disclosed herein shown in FIGS. 8, 19 and 20. Similar embodiments of the mobile bearing element forming a ball and socket bearing connection with the screw head are disclosed in US Patent Publications Nos. 2008/0161863 (Arnold I) and 2008/0161853 (Arnold II), the specifications of which are hereby incorporated by references in their entireties.

In one embodiment wherein the mobile bearing element forms a ball and socket connection with the screw head, and now referring to FIG. 8, a dynamic screw for a spine stabilization system comprises at least one bone anchor assembly 103 comprising a bone engaging member 105 and a receiver member 109. The bone engaging member may comprise a bone screw including a screw head retained within the receiver member and a screw shank extending from the receiver member. Mobile bearing element 111 disposed within the receiving member allows the screw head to be pivotably retained thereon. A flexible elongated connecting member 101 is connected to the receiving member. The elongated connecting member may be provided as a rod spanning between two or more bone anchor assemblies. The elongated connecting member is pivotably connected to the receiver member of the bone anchor assembly.

In another embodiment, a pivotable connection between the flexible elongated connection member and the receiver member is provided by a ball-shaped pivot member on the rod which engages a bearing surface provided within a cavity of the receiver member. Accordingly, the pivot point for the rod may be provided within the cavity in the receiver member. In one such embodiment, the rod may define an axis wherein the axis pivots about a pivot point on the axis when the rod pivots relative to the receiver member. In other embodiments, the pivot point of the rod is offset from the axis defined by the rod.

The flexible rod may be a fixed length or adjustable to accommodate different segmental units and patients of different sizes. In the adjustable embodiment, the rod comprises a shaft with a flexible central portion and at least one adjustable end. The adjustable end may be provided by various means. For example, the adjustable end may include a post configured to slide within the shaft of the rod. In one embodiment, the adjustable end is configured to threadably engage the shaft. In another embodiment, the adjustable end is comprised of a shape memory alloy.

When assembled, the spine stabilization system generally comprises at least two bone anchors with a rod extending between the two bone anchors. As mentioned above, each bone anchor includes a bone screw and a receiver member configured to retain the bone screw. The rod extends between the two receiver members. In one embodiment where the rod is fixed relative to the receiver members, the rod is adapted to bend when the receiver members move relative to one another. In another embodiment, the rod is pivotably connected to both the receiver members, and the rod is adapted to extend or compress when the receiver members move relative to one another.

In an alternative embodiment, one or more bone anchors of the spine stabilization system include an insert in the form of a retention member that acts to lock a bearing for the bone screw within the receiver member. To this end, the receiver member includes a screw head cavity and a rod cavity with an insert positioned between the screw head cavity and the rod cavity. The screw head cavity is configured to receive a bearing that engages the head of the bone screw with the screw shank extending from the receiver member. In one embodiment, the bone screw bearing is a split bearing. The insert is positioned between the rod cavity and the bearing member and is configured to secure the split bearing within the receiver member. The insert may be provided to fit within a groove formed in an interior sidewall of the receiver member. In this embodiment, the insert comprises a retaining ring that secures the split bearing within the screw cavity. In another embodiment, the insert is comprised of a compressible material positioned between the bearing member and the rod cavity. When the rod is positioned in the rod cavity, the insert is compressed against the bearing member, thus locking the bearing member within the screw cavity.

In yet another embodiment, the bone anchor assembly is configured with a low profile, wherein the rod is locked within the receiver member without the use of a fixation screw. In this embodiment, the bone anchor assembly includes a head and a screw shank extending from the head. The screw shank is pivotable with respect to the head. Furthermore, a rod cavity is formed within the head. The end of the rod includes features that lock the rod within the rod cavity when the rod is inserted into the rod cavity, thus connecting the rod to the head. For example, in one embodiment, the end of the rod comprises a plurality of fingers that may be flared to lock the rod within the rod cavity. The rod may also include a plurality of teeth that grasp or mesh with the rod cavity to further secure the rod within the cavity.

Therefore, in accordance with the present invention, there is provided a spine stabilization system comprising: a) a bone engaging member; b) a receiver member pivotably connected to the bone engaging member, the receiver member including a connecting member cavity and a bearing in contact with the bone engaging member; c) a flexible, elongated connecting member extending into the connecting member cavity of the receiver member; and d) a retention member positioned between the elongated connecting member and the bearing within the receiver member, the retention member configured to secure the bearing in place within the retention member.

The dynamic stabilization device, in particular for vertebrae, comprises a pair of mobile head polyaxial pedicle screws connected by a flexible rod disclosed herein. Mobile head polyaxial screws will toggle allowing motion, while preventing torque transmission to the screw bone interface. The flexible rod will be made of a material (such as a polymer such as PEEK) that is more compliant than traditional stiff metal rods in order to allow some bending, and will preferably include some internal reinforcement. Together the components will function as a complete dynamic stabilization system. Additionally, a modular system is also disclosed, which provides a surgical implant set containing a compliant polymer rod and a pair of mobile head polyaxial screws. Depending on the indications, the surgeon may choose to use one or both components to create a dynamic fusion or dynamic stabilization construct.

Therefore, the present invention contemplates the pairing of mobile head polyaxial screws with a reinforced flexible polymer rod to create a posterior dynamic stabilization (PDS) system. The toggle of the dynamic pedicle screws allows for change in the interpedicular distance during flexion and extension, and the flexible polymer rod flexes to accommodate vertebral body motion.

The dynamic polyaxial screw of the present invention prevents torque transmission to the screw-bone interface. A ball-and-socket (preferably, polymeric) component within the screw allows the shank to toggle with respect to the screw head, while the flexible rod locks to the receiving part The flexible polymer rod is generally a flexible composite rod, and in some embodiments, is reinforced for strength, with reinforcing fibers. The flexible polymer rod can be made from a number of flexible, biocompatible materials. Polymers such as PEEK, polycarbonate-urethane (PCU) and CFRP are among the preferred choices. The flexible polymer rod can be made from either neat polymers or from polymers supplemented with reinforcing fibers. However, in other embodiments the flexible rod may be made of metals, such as nitinol or titanium. The flexible polymer rod can be constructed with a variety of different cross-sections, which may be of constant or variable dimension. The reinforcement material can be located anywhere throughout the cross section of the flexible polymer rod to create the desired strength and flexibility. The flexibility may also vary depending on the axis of bend to provide stiffness in different ranges of motion. For example, a flexible polymer rod may be made stiffer in rotation than in flexion.

Composite flexible polymer rods having fiber reinforcements can be constructed in a variety of configurations to fine-tune strength and flexibility requirements of a particular device. The rod 113 shown in FIG. 9 may be constructed of various materials, including biocompatible polymers, metals or a combination thereof.

Figure 9:
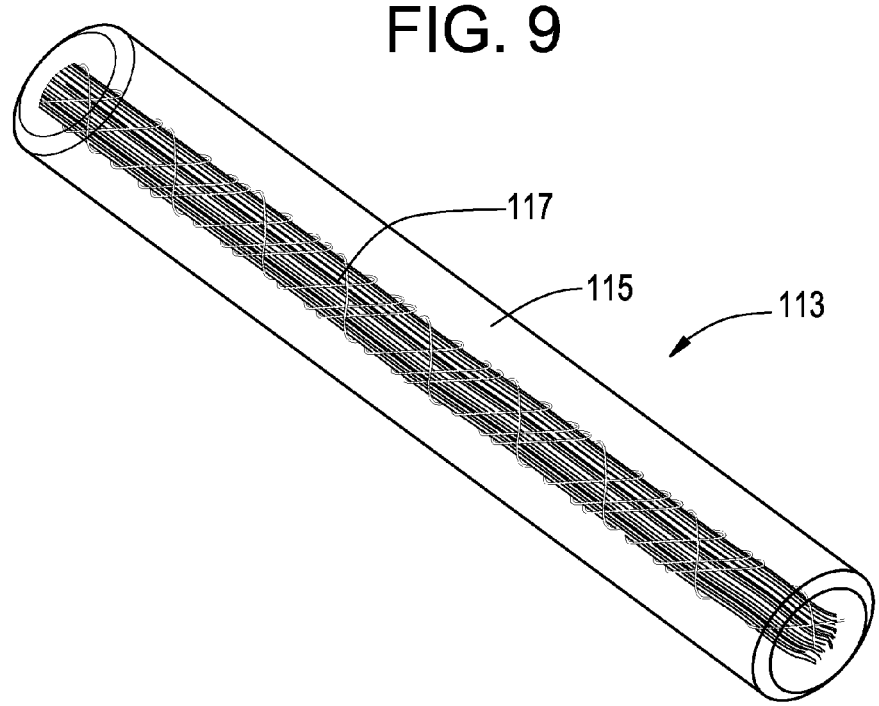
FIG. 9 through FIG. 18 disclose various flexible polymer rods having fiber cores.

The geometry shown here in FIG. 9 is not intended to limit the scope of the invention, but rather to show that flexible polymer rods can be created in a variety of configurations that allow bending and flexibility without fracture during a PDS device's life. The diameter of the central core reinforcement and the size of the reinforcement weave may be adjusted to change the rod's performance characteristics. The weave feature may also be accomplished by a waffle-like matrix or any other shape or orientation of fibers that would provide the same function without deviating from the concept. The weave and longitudinal fibers, although centered around the axis here in FIG. 9, may also be biased towards one side of the rod.

Figure 10:
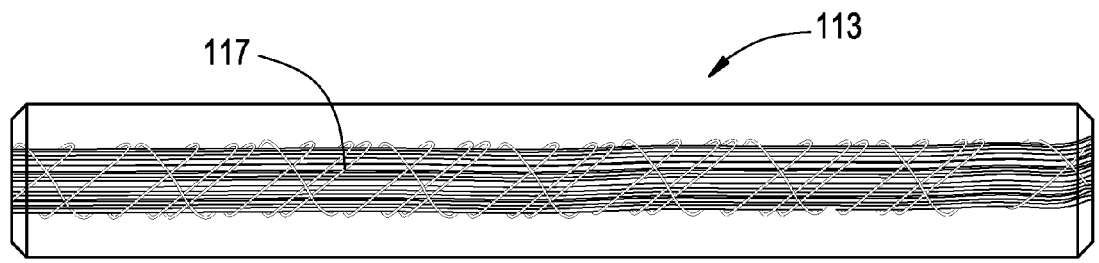

In preferred embodiments, the rod 113 of FIG. 9 comprises a polymer shell 115 typically made of PEEK) surrounding the central fiber core 117. FIG. 10 discloses a side view of the rod 113 of FIG. 9, detailing the weave of longitudinal fibers 117.

Figure 11:
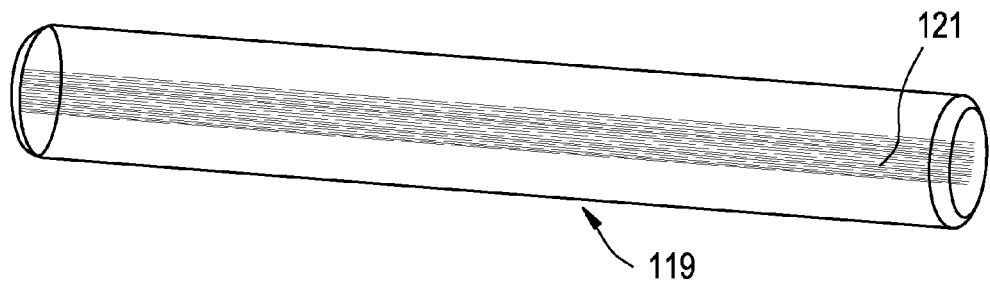

Now referring to FIG. 11, there is provided another embodiment in which rod 119 has longitudinal fiber core 121 in the absence of a weave.

FIGS. 12-18 disclose examples of the different orientations of the reinforcement material used to create the composite rod. The PEEK polymer material may be injection molded around the reinforcement material, or a polymer may be thermoset around the reinforcement matrix. Although a round rod cross-section is shown here in these FIGS., there is no limit to the type of rod cross section which could be used.

Figure 12:
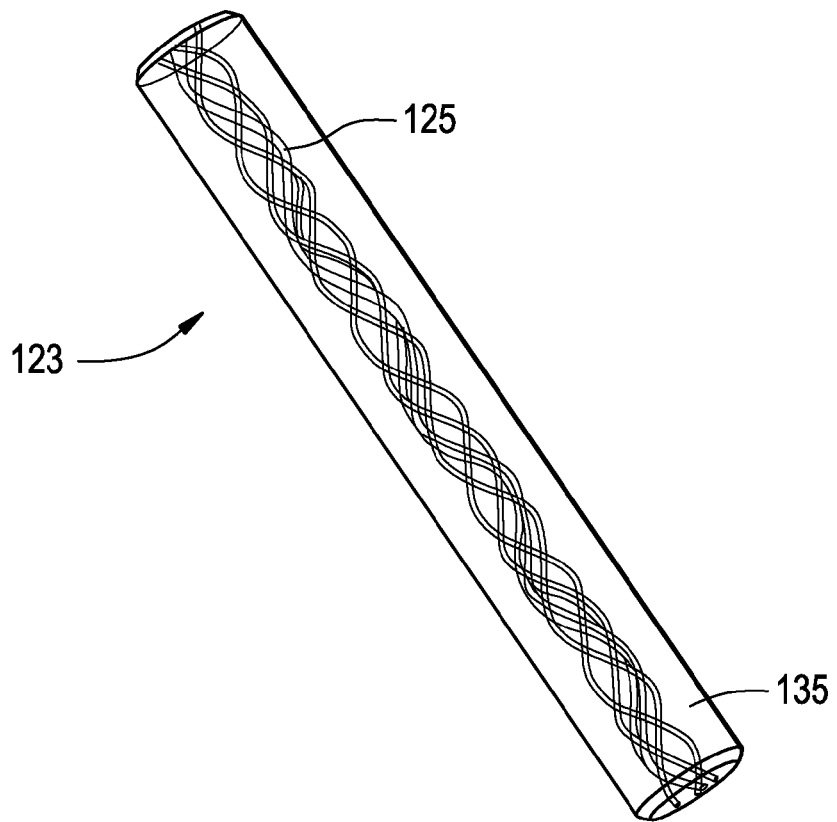
Figure 13:
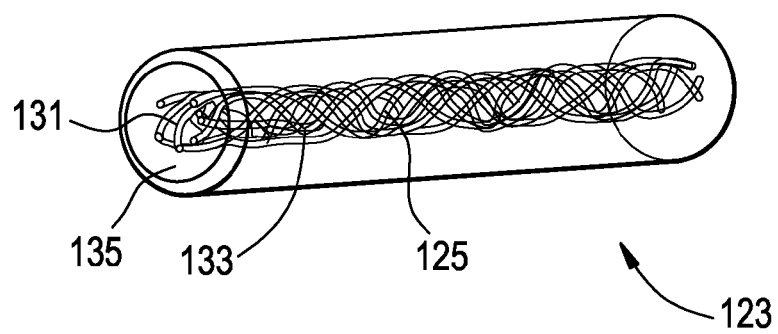

Now referring to FIGS. 12 and 13, there are provided various view of a rod 123 of the present invention having weaved fibers 125 located at an intermediate depth of the rod, thereby providing strength in flexion (tension). The fibers form a helical pattern, thereby forms an annular ring of fiber in cross section. The polymer jacket surrounding the fiber core allows flexibility and provides a clamping surface. Therefore, the cross section of the rod displays a polymer central portion 131, a fiber intermediate portion 133 and a polymer outer portion 135.

Figure 14:
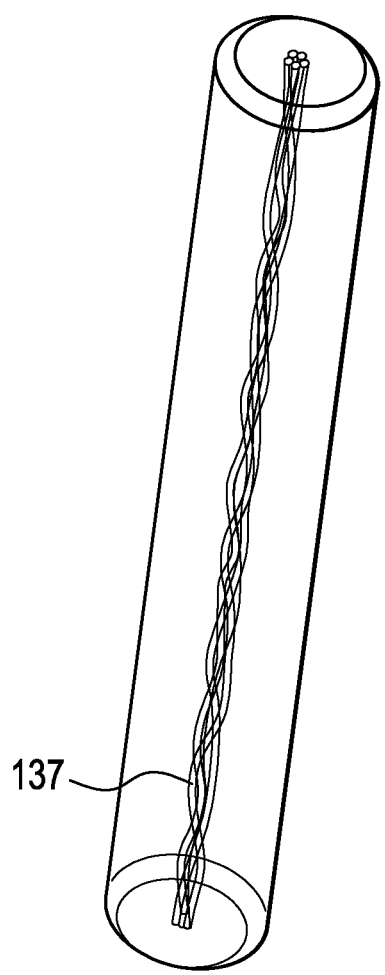

Now referring to FIG. 14, there is provided another embodiment of the rod of the present invention, wherein the fibers form a central braided core 137.

Figure 15:
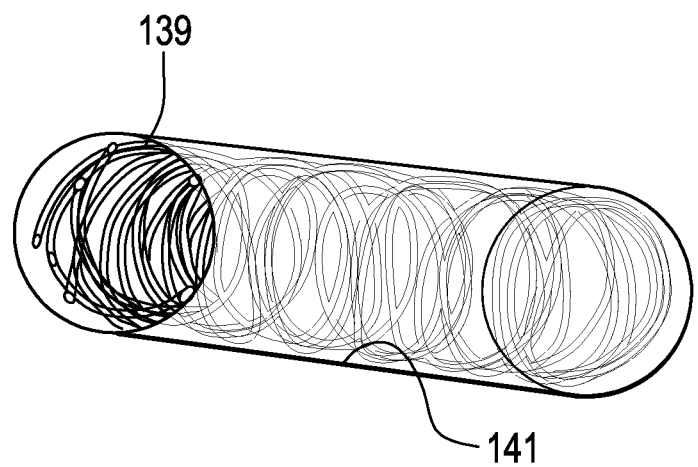
Figure 16:
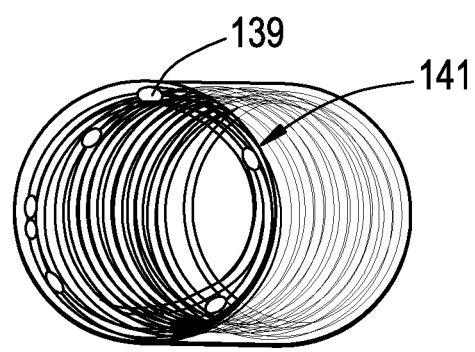

Now referring to FIGS. 15 and 16, there is provided another embodiment of the rod of the present invention, wherein the fibers form an annular ring 139 located just below the outer surface 141 of the rod. The fiber location is driven by the desired rod characteristics.

Figure 17:
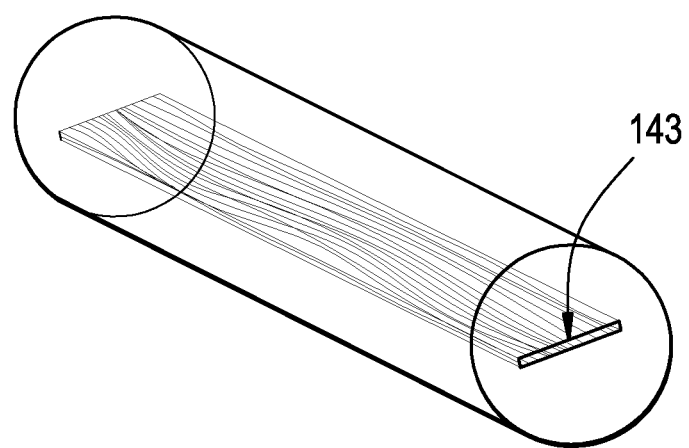
Figure 18:
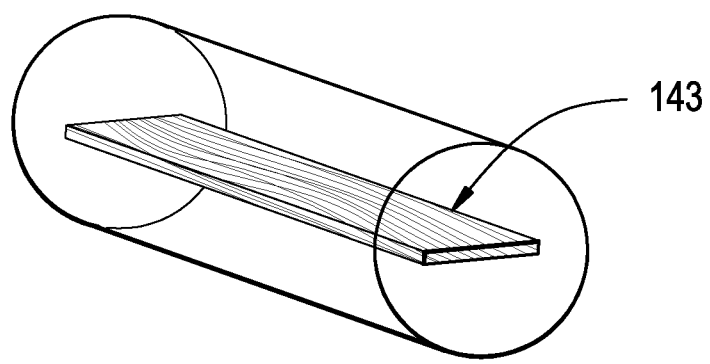

Now referring to FIGS. 17 and 18, there is provided another embodiment of the rod of the present invention, wherein the rod has a plane 143 of fibers oriented along the center of the rod to provide greater stiffness in response to certain motions. For example, this rod may allow more movement in flexion/extension, but less motion in lateral bending.

The two images provided in FIGS. 19 and 20 show translucency to better describe their functions: The bulk rod material 151 is semi-transparent to allow visualization of the internal reinforcement fibers, which provide strength. The top dynamic screw 153 shows translucency to allow better description of the internal function. The polymer insert bearing 155 surrounds the shank screw head 157 providing a mobile surface for the motion to occur. The rod locks to the titanium head. The rod 151 and screw 153 function together to allow posterior dynamic stabilization. The flexible polymer rod 151 bends as the screw head toggles, allowing for change in interpedicular distance.

The flexibility of the PDS system can be tweaked by changing the rod design and the range of motion within the dynamic polyaxial screw.

In some embodiments, the PDS system of the present invention improves torsional stability, as the mobile screw heads may only allow uniplanar motion/toggle. The mobile head screws also provide reduced screw-bone interface stresses as torque on the rod is not transferred to the screw shank.

In some embodimentsthe mobile head component of the present invention is substantially similar to the resilient mobile head component described in US Published Patent Application No. 2004/0225289 (Biedermann), the specification of which is incorporated by reference in its entirety.

Figure 23:
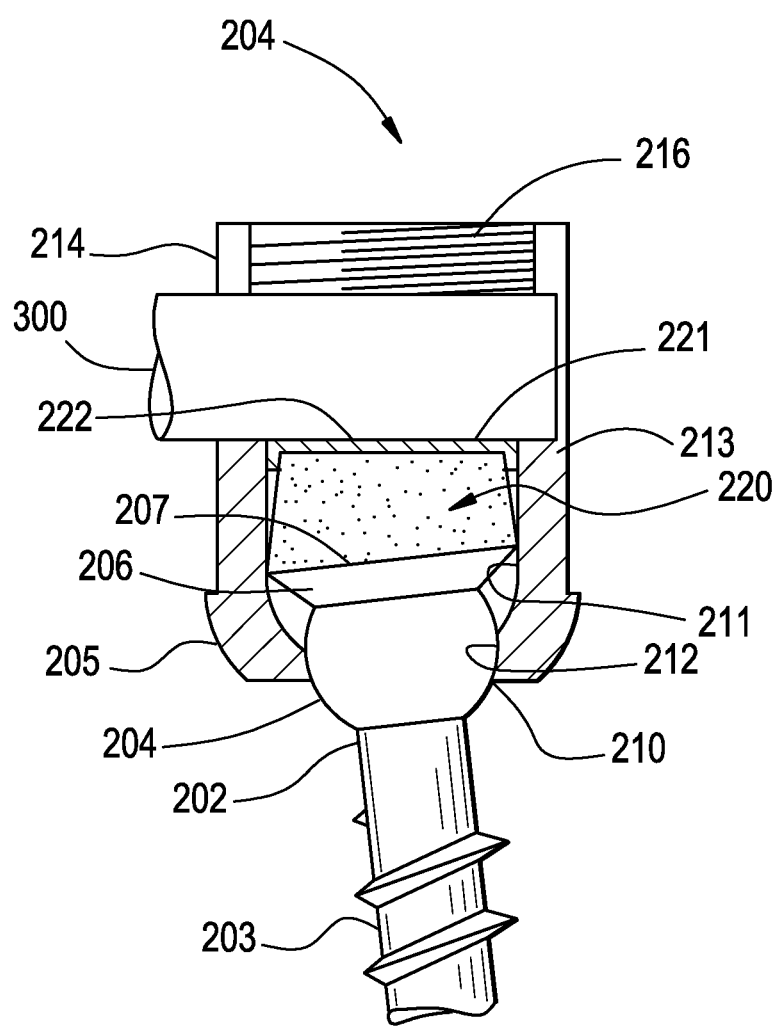
FIG. 23 shows an illustration in partial section of the anchoring device of FIG. 21 in the loaded state during the action of a force upon the anchoring element.

Now referring to FIGS. 21-23, in some embodiments of the present invention, the flexible rods 300 of the present invention are combined with a pair of dynamic anchoring devices 201. Preferably, each of these dynamic anchoring devices comprises i) a shank 203 for anchoring into a bone or a vertebra, ii) a head connected to the shank, iii) a receiving part 205 for the head and iv) a resilient (preferably, elastomeric) pressure element 220 acting on the head. The pressure element is formed and located in such a way that, upon a movement of the element from a first angular position of the shank relative to the receiving part into a second angular position, it exerts a return force on the head. Accordingly, the present invention includes a dynamic stabilization device, in particular for vertebrae. In such a stabilization device, the flexible rod is connected to two anchoring devices. At least one of the anchoring devices is constructed as a dynamic anchoring element.

Therefore, the present invention provides an anchoring device comprising an element having a shank for anchoring in a bone or a vertebra and a head connected to the shank, a receiving part for receiving the head, and a pressure element acting on the head, wherein the pressure element is resilient so that upon a movement of the element from a first angular position of the shank relative to said receiving part into a second angular position the pressure element exerts a return force onto the head to urge the element towards the first angular position.

Preferred embodiments of a bone anchoring element in accordance with the invention have one or more of the following features:

Preferably,—the resilient pressure element acts on the side of the head facing away from the shank and is formed of an elastomer. Preferably, the resilient pressure element comprises at least one spring element.

The device may also include a rigid element acting on the pressure element on a side of the pressure element opposite to the head. Preferably, the pressure element is substantially cylindrical and comprises a first section which is resilient and a second section which is rigid and which is located on a side opposite to the head; Typically, this second section comprises a U-shaped recess to receive a rod to be received in the receiving part, the recess forming two free legs and wherein a depth of the recess is greater than the diameter of the rod; Typically, the first section and the second section of the pressure element are separate parts. Preferably, the pressure element is formed by an insert made of an elastomer and has a support surface for the head to rest against. Preferably, the pressure element is pre-compressed by the rod when the rod lies on the bottom of the U-shaped recess. Preferably, the pressure element is arranged in the receiving part under pre-stress.

In some embodiments, there is a second elastic pressure element encompassing the head in a ring shape. This second pressure element may be shaped as O-ring or as a molded ring.

Preferably, the head comprises a flat surface on the side facing away from the shank and the resilient pressure element comprises a flat surface cooperating therewith. The head may comprise a spherical segment-shaped section adjacent to the shank and a collar on the side facing away from the shank. Preferably, the head and the shank are separate parts, wherein the head has a central axis and the shank is connectable to the head at a predetermined angle a to the central axis.

Preferably, the receiving part comprises a support surface to support the head, the support surface and/or the head being polished or coated to reduce friction.

Preferably, the receiving part comprises a U-shaped recess for inserting a rod and the pressure element is arranged between the head and the rod when the rod is inserted into the receiving part.

The invention also provides a dynamic stabilization device for bones, in particular for vertebrae, having at least two anchoring devices connected to a flexible polymer rod, wherein one of the anchoring devices is formed as the anchoring device described above.

Additionally, the invention provides a method for using the dynamic anchoring device and a method for stabilizing bones, in particular for stabilizing vertebrae, wherein the anchoring device is formed as the anchoring device described above.

As can be seen in particular from FIGS. 21 to 23, in accord with one embodiment of the invention, the dynamic anchoring element 201 is formed as a polyaxial screw. It comprises a screw element 202 with a threaded shank part 203 and a head 204 formed in one piece therewith and a receiving part 205. The head 204 is substantially formed in the shape of a segment of a sphere and has on its end opposite to the shank part 203 a widened edge or collar 206, so that a flat front face 207 is formed which has a diameter which is larger than the diameter of the spherical segment-shaped section of the head. A recess for bringing into engagement with a screwing-in tool is further formed in the front face 207.

The receiving part 205 is substantially formed cylindrically symmetric and has on one of its ends a coaxial first bore 210 the diameter of which is larger than that of the threaded section of the shank 203 and smaller than the spherical diameter of the spherical segment-shaped section of the head 204. It further has a coaxial second bore 211 which is open at the end opposite the first bore 210 and the diameter of which is large enough for the screw element 202 to be inserted through the open end with its threaded section through the first bore 210 and with the spherical segment-shaped section of the head 204 to the bottom of the second bore. In the receiving part, adjacent to the first bore 210 a section 212 is provided, shaped like a segment of a hollow sphere, the radius of which is substantially identical to the radius of the section of the spherical segment-shaped head 204. The receiving part further has a U-shaped recess 213, extending from the open end towards the first bore 210, the bottom of which is directed towards the first bore 210 and by which two open legs 214 are formed, only one of which is illustrated in the figures. An inner thread 215 is formed in the receiving part adjacent to the open end of the legs 214. The width of the U-shaped recess 213 is minimally larger than the diameter of a rod 300 to be received therein which connects several such polyaxial screws. The depth of the U-shaped recess is dimensioned in such a way that when the rod is inserted a fixing screw 216 can be screwed in between the legs.

The section 212 of the receiving part which is shaped like a segment of a hollow sphere is preferably polished smooth or coated with a material which increases the sliding capacity, so the head 204 can easily be swiveled in the section 212 of the receiving part. Alternatively, or additionally the head 204 is polished smooth or coated.

Between the inserted rod 300 and the head 204 of the screw element a pressure element 220 is provided. The pressure element 220 is formed in the shape of a cylinder and has a diameter which is smaller than the inner diameter of the second bore 211 of the receiving part and which is preferably identical to the diameter of the front face 207 of the head. The axial length of the pressure element 220 is slightly larger than or identical to the distance between the front face 207 of the head 204 and the bottom of the U-shaped recess 213 in the inserted state. The pressure element is resilient, in the illustrated embodiment it is formed from an elastomer, e.g., from polyurethanes or polysiloxanes. However, any suitable biocompatible material can be used.

Between the pressure element 220 and the inserted rod 300 a cap 221 is provided, which covers the pressure element on the side facing the rod and which is constructed from an inflexible material, for example a synthetic material or a body-compatible metal. The outer diameter of the cap 221 is dimensioned in such a way that the cap is displaceable by sliding in the second bore of the receiving part and the inner diameter of the cap substantially corresponds to the outer diameter of the pressure element 220 when this is in an unloaded state. The cap overlaps the pressure element to such an extent that the pressure element is able to expand in the radial direction when put under load.

FIG. 21 shows the unloaded state in which the screw element 202, the pressure element 220 and the cap 221 are inserted into the receiving part and the rod 300 is placed into the U-shaped recess 213, but the inner screw has not yet been screwed down. In this state the side 222 of the cap 221 facing away from the pressure element 213 is at a slightly higher position than the bottom of the U-shaped recess 213, so that the rod rests with its lower side on the surface 222 of the cap and thus a gap 213 is formed between the lower side of the rod and the bottom of the U-shaped recess 213.

In operation, as shown in FIG. 21, first the screw element 202 is inserted into the receiving part 205 from the open end thereof until the head rests against the section 212 of the receiving part shaped like a segment of a hollow sphere. The screw element is then screwed into the vertebra. Then, the pressure element 220 together with the cap 221 placed thereon is inserted into the receiving part, the receiving part is aligned and the rod inserted. Finally, the inner screw 216 is screwed into the receiving part.

As illustrated in FIG. 22, the inner screw is screwed in until it presses the rod against the bottom of the U-shaped recess and thus fixes the rod. At the same time, the rod presses on the cap 221, which serves for even distribution of the force of pressure exerted by the rod on to the entire surface of the pressure element. Due to the elasticity of the pressure element it is pre-compressed via the force exerted by the rod. At the same time, the pressure element takes on a shape curved outwards in the radial direction, shown in FIG. 22. In the state shown in FIG. 22 the pressure element 220 is under bias in respect of the screw head 204 and due to the return force it presses with its lower side evenly on the front face 207 of the head. In this way, the head is pressed against the section 212 of the receiving part.

The screw element 202 screwed into the vertebral body is moved out of its resting position by a self-movement of the vertebral column. When the vertebra moves towards the rod at an angle of 90° to the rod axis there is uniform compression of the pressure element and the angle of the shank relative to the receiving part does not change. When the vertebra moves at an angle other than 90° to the rod axis, as shown in FIG. 23, there is a swiveling of the head, which easily slides in the section 212 of the receiving part. Thereby, the front face 207 of the screw head exerts a compression force on to the pressure element on one side which compresses it on one side near the edge. On the other hand, on the opposite side, the pressure element standing under pre-stress expands owing to the relief of pressure. Thus, the pressure element always remains in contact with the screw head.

Due to the elasticity of the pressure element, the compression effects a return force onto the screw head. In this way, a movement of the vertebra back into its original position in which it has been placed by the surgeon is supported.

By the choice of an elastomer material for the pressure element with a desired compressibility a limitation of motion of the vertebra can be adjusted. If the material is only slightly compressible, the device allows only a small deflection out of the resting position. If the material properties are changed, larger swivel ranges are possible. Those skilled in the art can readily substitute materials using routine experimentation. Body-compatible elastomer can be used as elastomer material, e.g., polyurethanes or polysiloxanes.

The swivel range can also or additionally be set by the selection of the diameter of the collar 206 of the screw head relative to the diameter of the second bore 211 of the receiving part. When the collar 206 abuts on the wall of the receiving part in the swiveled position of the screw element 202, no further swiveling is possible.

We claim:

1. A spinal pedicle rod comprising an internally reinforced polymeric core that is at least partially encased within a polymeric coating, wherein the core comprises a weave of fibers,
   the rod further having a pair of end portions, and an intermediate section therebetween, wherein the core of the intermediate section has a base section and a rib extending from the base section,
   wherein the core is at least partially encased within a polymeric coating having an outer surface, and the rib extends through the outer surface of the coating.

2. The rod of claim 1 wherein the core has a non-circular axial cross-section.

3. The rod of claim 2 wherein the core has a semi-oval axial cross-section.

4. The rod of claim 2 wherein the core has an axial cross-section having a height and a width, wherein the height is greater than the width.

5. The rod of claim 1 wherein the core is substantially fully encased within the polymeric coating.

6. The rod of claim 1, wherein the core comprises continuous fiber reinforcements.

7. The rod of claim 6 having a longitudinal axis, wherein the continuous fiber reinforcements align themselves within the core along the longitudinal axis of the rod.

8. The rod of claim 1 wherein the rib extends through a concave surface of the coating.

* * * * *